(12) United States Patent
Lithgow

(10) Patent No.: US 10,368,770 B2
(45) Date of Patent: Aug. 6, 2019

(54) NEURAL EVENT PROCESS

(75) Inventor: Brian John Lithgow, Ormond (AU)

(73) Assignee: Monash University, Victoria (AU)

( * ) Notice: Subject to any disclaimer, the term of this patent is extended or adjusted under 35 U.S.C. 154(b) by 1547 days.

(21) Appl. No.: 11/661,622

(22) PCT Filed: Sep. 1, 2005

(86) PCT No.: PCT/AU2005/001330
§ 371 (c)(1),
(2), (4) Date: Oct. 9, 2007

(87) PCT Pub. No.: WO2006/024102
PCT Pub. Date: Mar. 9, 2006

(65) Prior Publication Data
US 2008/0167570 A1    Jul. 10, 2008

(30) Foreign Application Priority Data
Sep. 1, 2004  (AU) .............................. 2004904995

(51) Int. Cl.
| | |
|---|---|
| *A61B 5/02* | (2006.01) |
| *A61B 5/0476* | (2006.01) |
| *A61B 5/048* | (2006.01) |
| *A61B 5/0484* | (2006.01) |
| *A61B 5/16* | (2006.01) |
| *A61B 5/00* | (2006.01) |
| *A61B 5/0496* | (2006.01) |

(52) U.S. Cl.
CPC ............ *A61B 5/0476* (2013.01); *A61B 5/048* (2013.01); *A61B 5/04845* (2013.01); *A61B 5/165* (2013.01); *A61B 5/4082* (2013.01); *A61B 5/6814* (2013.01); *A61B 5/7239* (2013.01); *A61B 5/0496* (2013.01)

(58) Field of Classification Search
CPC ........................... A61B 5/0476; A61B 5/0496
USPC .................................................. 600/544–545
See application file for complete search history.

(56) References Cited

U.S. PATENT DOCUMENTS

| | | | | |
|---|---|---|---|---|
| 5,003,986 | A * | 4/1991 | Finitzo et al. ................ | 600/544 |
| 6,658,287 | B1 * | 12/2003 | Litt et al. ...................... | 600/544 |
| 2002/0059159 | A1 * | 5/2002 | Cook ............................. | 706/62 |
| 2003/0181821 | A1 * | 9/2003 | Greenwald et al. .......... | 600/544 |
| 2005/0070774 | A1 * | 3/2005 | Addison et al. ............... | 600/323 |

FOREIGN PATENT DOCUMENTS

| | | |
|---|---|---|
| JP | 2002-502270 | 1/2002 |
| WO | WO 97/26823 | 7/1997 |

(Continued)

OTHER PUBLICATIONS

"Clinical Electrocochleography: Overview of Theories, Techniques and Applications" by John A. Ferraro, Nov. 15, 2000.*

(Continued)

*Primary Examiner* — Puya Agahi
(74) *Attorney, Agent, or Firm* — Merchant & Gould P.C.

(57) ABSTRACT

A neural event process, including receiving a neural response signal, decomposing the signal using at least one wavelet, differentiating phase data of the wavelets and the response signal to determine maxima and minima of the phase data and the signal, and processing the maxima and minima to determine peaks representing neural events.

30 Claims, 21 Drawing Sheets

(56) References Cited

FOREIGN PATENT DOCUMENTS

| WO | WO 2002/047547 | 6/2002 |
|---|---|---|
| WO | WO 2004/105601 | 12/2004 |

OTHER PUBLICATIONS

"Meniere's Disease" by Olivier Sterkers, E. Ferrary, R. Dauman, P. Sauvage, Patrick Tran Ba Huy, pp. 745, 1999.*
"Artifact reduction in electrogastrogram based on empirical mode decomposition method" by Liang et al., Medical & Biological Engineering & Computing, vol. 38, pp. 35-41, 2000.*
"Fourier-, Hilbert-and wavelet-based signal analysis: are they really different approaches?" by Bruns, Journal of Neuroscience Methods, V. 137, pp. 321-332, Mar. 2, 2004.*
http://www.bioon.com/bioline/neurosci/course/audvest.html, 2002.*
Japanese Office Action for corresponding JP 2007-528527 dated Aug. 2, 2011.
Hall III. *Handbook of Auditory Evoked Responses*. Needham Heights, MA., Allyn and Bacon. 1992.
Bradley et al. "On Wavelet Analysis of Auditory Evoked Potentials." *Clinical Neurophysiology*. vol. 115. 2004. pp. 1114-1128.
Quiroga et al. "Wavelet Transform in the Analysis of the frequency composition of evoked potentials." *Brian Research Protocols*. vol. 8. 2001. pp. 16-24.

* cited by examiner

NEURAL EVENT PROCESS

FIELD

The present invention relates to a neural event process and a system for performing the process. The process may advantageously be used to extract data representing a response produced by a patient's auditory or vestibular system.

BACKGROUND

Systems have been developed to obtain an auditory evoked response (AER) or brainstem auditory evoked response (BAER) for a patient representing activity of the patient's auditory system. The AER is an electrical brain wave or neural response obtained from electrodes placed on the patient in response to a stimulus, normally a sound. Depending of the latency of the response and the placement of the electrodes, different classes or types of AERs can be obtained. Those with the shortest latency are generated by the inner ear and the auditory nerve, and are referred to as electrocochleography responses. The next response reflects activity within the auditory brainstem and is referred to as an auditory brainstem response (ABR). Further detail is provided in Hall, James W, III; Handbook of Auditory Evoked Responses; Allyn and Bacon; Needham Heights, Massachusetts, 1992.

Electrocochleography ("ECOG" or "ECochG") systems are currently used to perform diagnoses of the cochlea and vestibular apparatus. In the case of the vestibular system, recently analysis for this specific part of the ear has been referred to as electrovestibulography (EVestG), being a specific sub-class of ECOG. The systems are used to produce a patient neural response which involves placing a recording electrode as close as practical to a patient's cochlea. An acoustic transducer, eg an earphone, is used to provide an auditory stimulus to evoke the response. For EVestG the patient is however tilted, in different directions, to evoke a specific response from the vestibular apparatus. It is not necessary to also use an auditory stimulus for EVestG. An ECOG signal representing the neural response is used to determine an Sp/Ap ratio that can be used for the diagnosis of a number of conditions, particularly Meniere's disease. The first wave, normally labelled N1, of the response signal is examined to determine the summating potential (Sp), the action potential (Ap) and the second summating potential (Sp2), as shown in FIG. 1. The response is only of the order of a few µV and is received with considerable unwanted noise making it difficult to determine and isolate.

For example, the ECOG signal is normally assessed by obtaining multiple samples from a patient in response to acoustic stimuli, and then obtaining an average Sp/Ap ratio for diagnosis. This process, however, is neither very sensitive nor specific, as a patient can have Meniere's disease and a normal ECOG, and alternatively the patient could also have an abnormal ECOG, but not have Meniere's disease. Accordingly, an alternative process ("the Franz process") has been developed by Professor Burkhard Franz, as described in International Patent Publication WO 02/47547, which seeks to analyse directly the vestibular response, rather than the cochlea response, as Meniere's disease is a pathology of the vestibular system. The Franz process uses an ECOG system to record the response obtained from a patient asked to tilt their head either forward, backward, contralaterally or ipsilaterally. The process seeks to identify a periodic signal in the response which is believed to come from either the semi-circular canals (SCCs) or the otolith organs at predominantly 23 Hz, but also at 11.5 Hz and 46 Hz. This analysis is done by averaging the ECOG response over a number of intervals at the frequency of interest, eg $\frac{1}{23}$ Hz at repeated intervals.

There are, however, a number of difficulties with the Franz process. Firstly, the process is not considered to be reliable for all patients, and particularly for inhibitory head tilts and especially for involuntary head tilts. The process also cannot be easily adopted by an audiologist without significant training. Also, more significantly, it has been found that the frequencies of interest, 11.5, 23 and 46 Hz, do not have characteristic signals that can be reliably located once the background signal for ambient noise has been removed. This indicates that these frequency components of the ECOG response are primarily induced by background noise and/or muscle (premotor and/or motor) activity, and any response from the SCCs and otolith organs is extremely difficult to detect or isolate at these frequencies. Similar problems exist with determining and analysing other AERs, such as the ABR.

Accordingly, it is desired to address the above, or provide at least a useful alternative.

SUMMARY

In accordance with the present invention there is provided a neural event process, including:
   receiving a neural response signal;
   decomposing said signal using at least one wavelet;
   differentiating phase data of said wavelets and said response signal to determine maxima and minima of said phase data and said signal; and
   processing said maxima and minima to determine peaks representing neural events.

The present invention also provides a neural event process, including:
   receiving a neural response signal produced by an ECOG system;
   decomposing said signal into at least one wavelet representing a centre frequency having a low frequency in the spectrum of said signal, said wavelet having a small bandwidth factor;
   differentiating phase data of said wavelet and said response signal to determine maxima and minima of said phase data and said signal; and
   processing said maxima and minima to determine an Sp/Ap ratio.

The present invention also provides an auditory brain stem response (ABR) process, including:
   receiving an ABR signal produced by an ABR system;
   decomposing said signal into at least one wavelet representing a centre frequency having a low frequency in the spectrum of said signal, said wavelet having a small bandwidth factor;
   differentiating phase data of said wavelet and said response signal to determine maxima and minima of said phase data and said signal; and
   processing said maxima and minima to determine Sp and Ap data.

The present invention also provides a system for performing the process.

The present invention also provides a computer readable medium having computer program code for use in performing the process.

The present invention also provides a neural response system, including:
  electrodes for connecting to a person to obtain a neural response signal;
  an amplifier for receiving and producing a sampled form of said signal for processing; and
  an analysis module for decomposing said signal using at least one wavelet, differentiating phase data of said wavelets and said response signal to determine maxima and minima of said phase data and said signal, and processing said maxima and minima to determine peaks representing neural events.

The present invention also provides a neural response system, including:
  electrodes for connecting to a person to obtain a neural response signal;
  an amplifier for receiving and producing a sampled form of said signal for processing; and
  an analysis module for processing said signal to generate a TAP marker to indicate whether a person has a disorder.

The present invention also provides a neural response system, including:
  electrodes for connecting to a person to obtain a neural response signal;
  an amplifier for receiving and producing a sampled form of said signal for processing; and
  an analysis module for processing said signal to generate plot of time and frequency data for peaks in the 70 to 300 Hz range to display activity of components of a person's auditory system and mark any disorder.

The present invention also provides a neural response process, including processing a response signal obtained from a person to generate a TAP marker to indicate whether said person has a disorder.

The present invention also provides a neural response process, including processing a response signal obtained from a person signal to generate plot of time and frequency data for peaks in the 70 to 300 Hz range to display activity of components of a person's auditory system and mark any disorder.

BRIEF DESCRIPTION OF THE DRAWINGS

Preferred embodiments of the present invention are hereinafter described, by way of example only, with reference to the accompanying drawings, wherein.

DETAILED DESCRIPTION OF PREFERRED EMBODIMENTS

Figure 2:
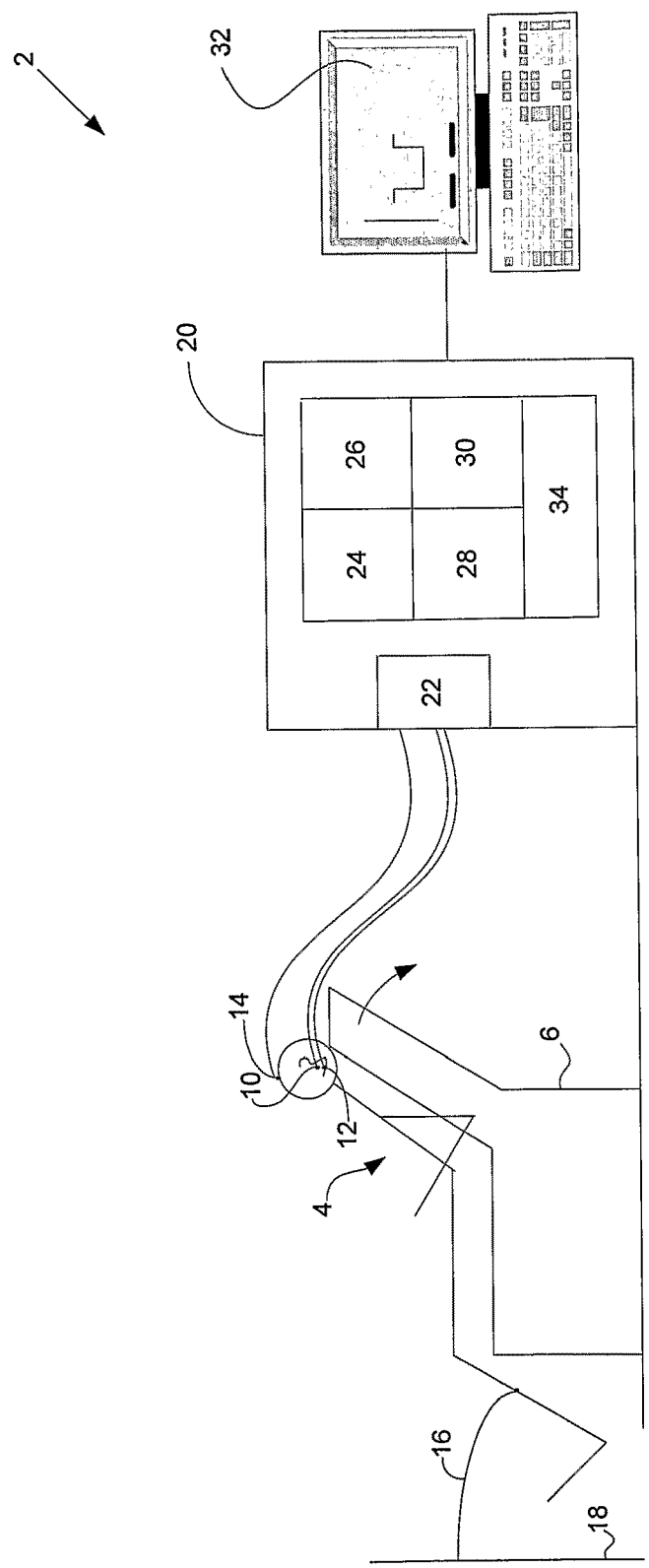
FIG. 2 is a schematic diagram of a preferred embodiment of an ECOG system connected to a patient.

An ECOG system 2, as shown in FIG. 2, is used to obtain Sp/Ap plots, as shown in FIGS. 5 to 10, from a patient who is subjected to a single stimulus, eg an involuntary head tilt. The Sp/Ap plots are generated from the ECOG signal produced in response to the stimulus. The ECOG signal is obtained from electrodes 10, 12 and 14 electrically connected to an amplifier circuit 22 of a computer system 20 of the ECOG system 2. A first electrode 10 (eg a ECochG Electrode produced by Bio-Logic Systems Corp is placed on the tympanic membrane of an ear of a patient 4. A second electrode 12 is placed on the patient's earlobe, as a reference point, and a third electrode 14 is connected to the patient's forehead and to the common point of the amplifier. A shield connection 16 is also made to an electrical isolation shield 18 normally placed around the testing room. The shield 18 is connected to the shield of the amplifier 22. To obtain an auditory ECOG signal a continuous auditory signal is applied to the ear, comprising alternating polarity acoustic clicks. However, for a vestibular ECOG signal (ie a EVestG signal) the patient 4, as shown in FIG. 2, is placed on a chair 6, such as a recliner lounge chair, that allows the patient's head to be tilted either voluntarily or involuntarily. Tilt chairs have been specifically produced by Neuro Kinetics Inc. that enable a patient to be tilted and produce a response to this stimulus which is less corrupted by muscle artefact. An involuntary head tilt is obtained by an assistant manipulating the chair 6 so as to induce the head tilt without any patient neck muscle activity. A typical sequence is 20 seconds in a neutral position, 20 seconds tilted and 20 seconds neutral when tilted back up. The head tilt is done for approximately the same angle as a maximum voluntary head tilt that could be achieved by the patient themself. Tilts are back, forward, ipsilateral and contralateral. Though less effective and less location specific, it is, however, also possible for the EeOG system 2 to produce Sp/Ap plots derived from a response from the combined auditory and vestibular system that is produced without any specific stimulus. This is based on recorded spontaneous background activity of the auditory and vestibular system. For a voluntary head tilt, to obtain a stimulated response, the patient is asked to sit in the chair upright with their head in the neutral position for 20 seconds, and then their head tilted forward for 20seconds, back to neutral for 20 seconds, backwards again for 20 seconds, neutral for 20 seconds, ipsilateral to the electrode 10 for 20 seconds, neutral for 20 seconds, contralateral to the electrode 10 for 20 seconds and then neutral for 20 seconds.

Figure 3:
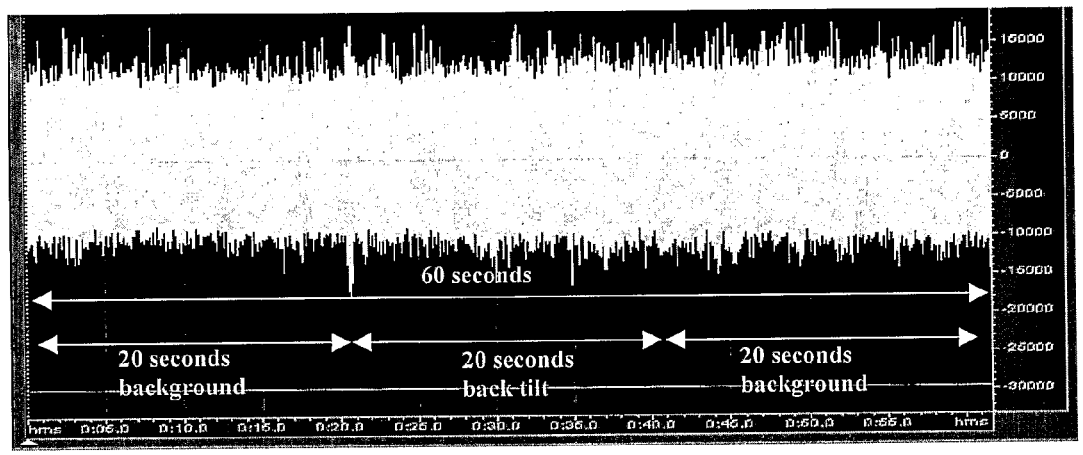
FIG. 3 is a response signal recorded by the system.

The neural response produced on electrodes 10 to 14 is continuously recorded by the ECOG system 2. The neural response signal for each tilt is a time domain voltage signal having multiple frequency components. The main components of interest are up to 22,500 Hz, and accordingly the sampling rate used by the system 2 is chosen to be 44.1 kHz. With this rate the Sp peak (depending on the signal to noise ratio (S/N)) is only a few samples wide. The signal is characterised by distinct regions in time: (i) a background region comprising primarily background ambient noise; (ii) an onset region for the start of tilt (approximately 0-5 seconds after tilt onset) which includes the response of the semi circular canals and otolith organs; (iii) a transient region for the remainder of the tilt (approximately 5-10 seconds after tilt onset) which includes the response of the semi circular canals (decaying) and otolith organ; and (iv) a steady state region (approximately 10-20 seconds after tilt onset) which includes essentially the response of the otolith organs. An example of a recorded response signal for an involuntary tilt is shown in FIG. 3, and the elements of the signal are described in the table below

| Tilt Segment | Time (sec) |
|---|---|
| Background | 5-20 |
| Onset | 20-25 |
| Transient | 20-30 |
| Steady state | 30-40 |
| Onset (tilting back up) | 40-45 |
| Transient (tilting back up) | 40-50 |
| Steady state (tilting back up) | 50-60 |

Figure 4:
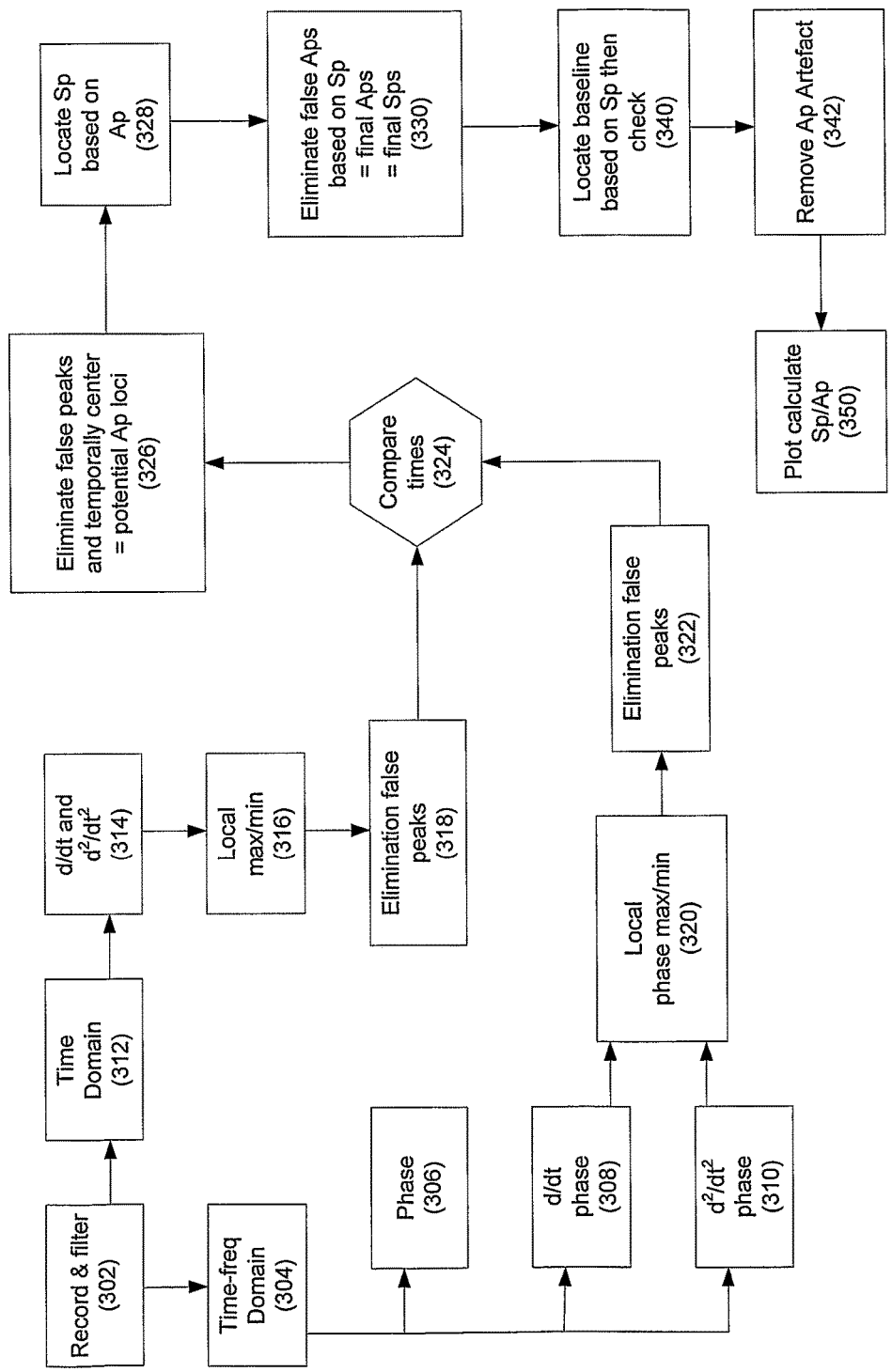
FIG. 4 is a flow diagram of a neural event process performed by the ECOG system.
Figure 13:
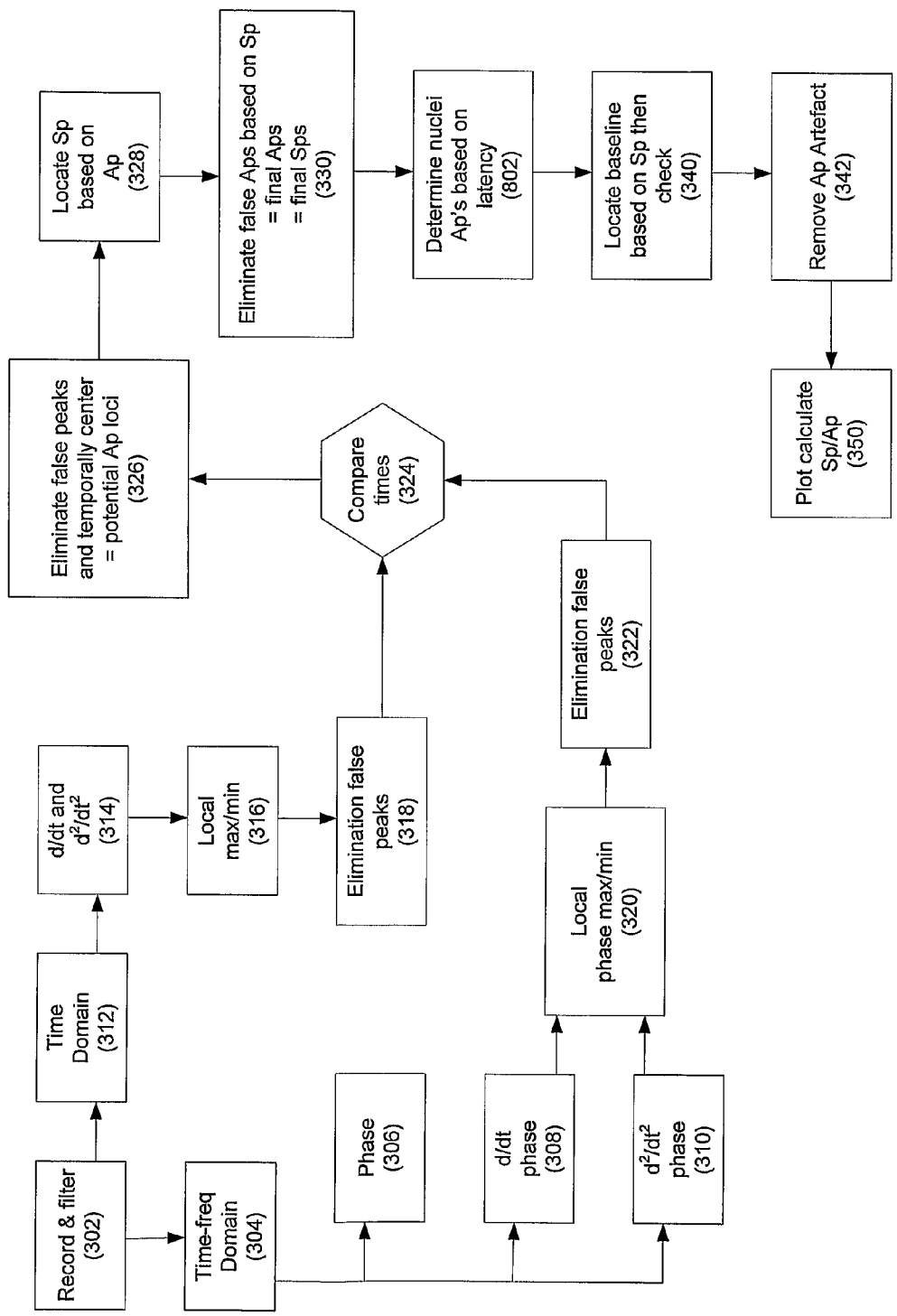
FIG. 13 is a flow diagram of a neural event process performed by a preferred embodiment of an ABR system connected to a patient.

The computer system 20 of the ECOG system 2 includes the amplifier 22 and a communications module 24 for handling the output of the amplifier 22 and then storing the response as a voltage signal over time as a wave file using a computer program such as Adobe Audition provided by a capture module 26. The amplifier 22 includes a CED 1902 isolated pre-amplifier and a CED Power 1401 analogue to a digital converter (ADC). Both the CED 1902 and CED 1401 ADC are produced by Cambridge Electronic Design Limited. The CED 1401 ADC has an excellent low frequency (less than a few Hz) response. The computer system 20 has further software modules, including an analysis module 28 and a display module 30. The analysis module 28 includes computer program code (eg. MATLAB® code) responsible for performing neural event extraction processes, as shown in FIGS. 4 and 13, in conjunction with the other software modules. The analysis module 28 also executes a number of different filters used to filter the response signal samples, as discussed below. The graphics display module 30 generates a user interface 32 for an operator of the ECOG system 2 to provide input controls so that the operator can control the neural event extraction process, and to generate displays of neural event data, such as the Sp/Ap plots shown in FIGS. 5 to 10. The computer program code of the software modules 24 to 30 of the computer system 20 are run on an operating system 34, such as Microsoft Windows or Linux, and the hardware used may include the amplifier 22 and a standard personal computer 20, such as that produced by IBM Corporation. ECOG recording systems are produced by Bio-Logic Systems Corp. Whilst the neural event extraction process may be performed under the control of the software of the modules 24 to 34, it will be understood by a skilled addressee that steps of the process can be performed by dedicated hardware circuits, such as ASICs and FPGAs, and also performed by components or modules distributed across a computer communications network, such as the Internet.

The neural event extraction process uses known temporal and frequency characteristics of an Sp/Ap plot to try to accurately locate an evoked response from the patient. Basically only a rough shape of the plot and the expected latency between the points of interest is known. Latency between the points corresponds to a frequency range of interest. Accordingly, the Sp/Ap plot is known to exhibit a large phase change across a frequency range of interest at points on the Sp/Ap plot, in particular, the Sp, Ap, onset of Sp, offset of Ap and beginning of Sp2 points. The neural event extraction process operates to produce a representative data stream that can be used to determine neural events occurring in the right time frame and with appropriate latency that can be considered to constitute characteristic parts of an evoked response. The same principle can also be applied to other AERs, as discussed below.

Figure 11:
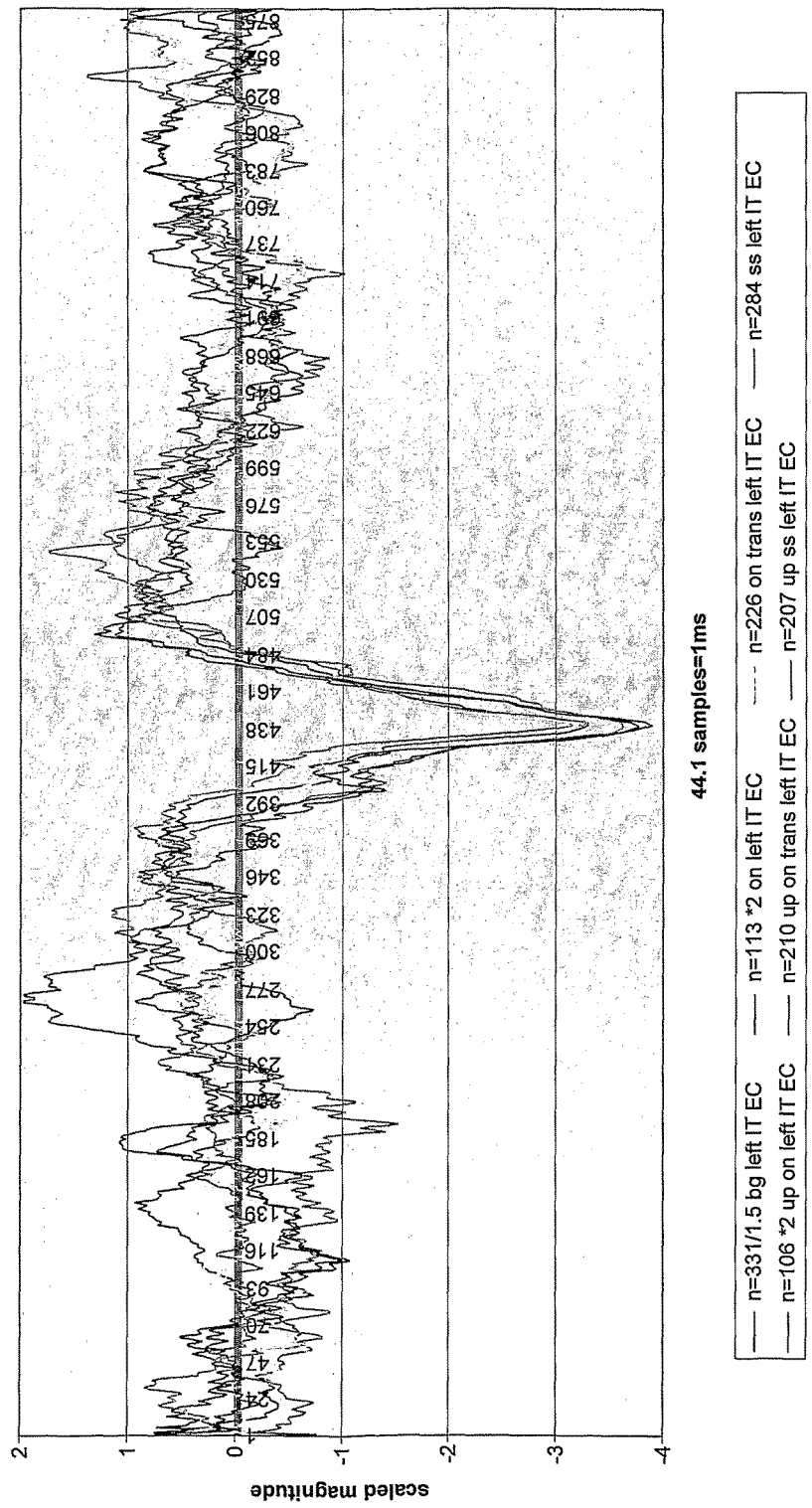
FIG. 11 is a display of Sp/Ap plots produced using a high pass filter by the ECOG system.
Figure 12:
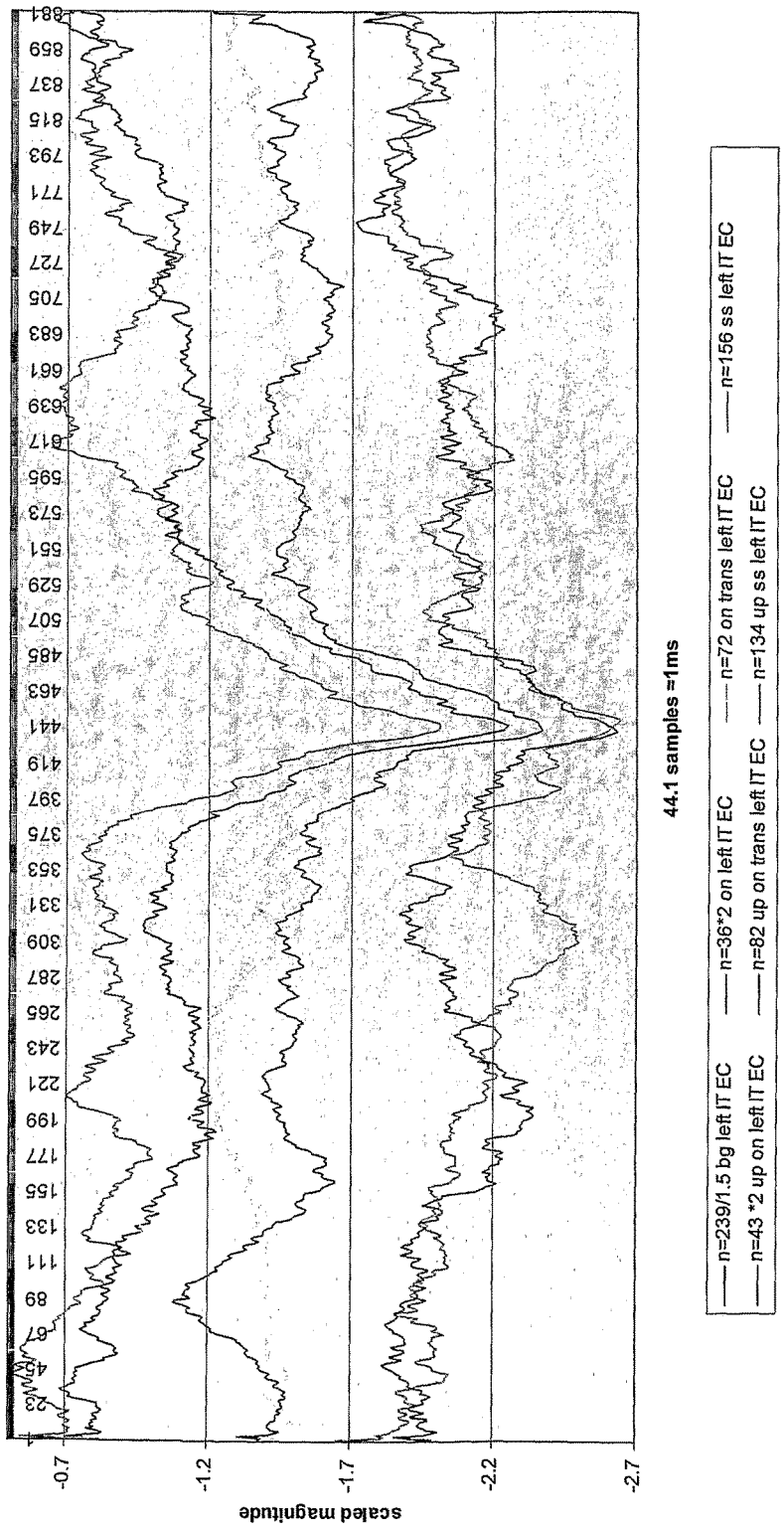
FIG. 12 is a display of Sp/Ap plots produced by the ECOG system by including DC offsets of the stimulus response.

The neural event extraction process, as shown in FIG. 4, involves recording the voltage response signal output by the amplifier 22 in response to a head tilt (step 302). Where necessary a 50 or 60 Hz mains power notch filter is applied to the recording in the amplifier stage to remove power frequency harmonics. The response signal from the amplifier 22 may also be high pass filtered (for example by a 120 Hz 1 pole Butterworth filter) to enable the extraction process to generate improved Sp/Ap peak plots (eg as shown in FIG. 11) at step 350. If the very low frequency data is retained, ie<10 Hz, then this can be used to plot (at step 350) discriminate "dc" magnitude threshold shifts prior to a neural event. These threshold shifts are shown in FIG. 12 and relate to the onset region (largest shift and therefore at the bottom of FIG. 12), the transient region (next largest shift) and the steady state region (lowest shift and at top). Examination of this very low frequency data, and in particular the magnitude shifts, can be used to aid the diagnosis of central nervous system disorders, as described below, and in particular illustrate more cortical influences on the vestibular system. Absence or enhancement of the shifts tend to indicate a disorder.

The recorded response signal is decomposed in both magnitude and phase using a complex Morlet wavelet (step 304) according to the definition of the wavelet provided in equation (1) below, where t represents time, $F_b$ represents the bandwidth factor and $F_c$ represents the centre frequency of each scale. Other wavelets can be used, but the Morlet is used for its excellent time frequency localisation properties. The neural response signal x(t) is convolved with each wavelet.

$$\psi \text{ Morlet}(t) = \frac{1}{\sqrt{2\pi F_b}} e^{j2\pi F_c t - \frac{t^2}{2F_b}} \quad (1)$$

To directly measure the vestibular system, seven scales are selected to represent wavelets with centre frequencies of 12000 Hz, 6000 Hz, 3000 Hz, 1500 Hz, 1200 Hz, 900 Hz and 600 Hz. Different frequencies can be used provided they span the frequency range of interest and are matched to appropriate bandwidth factors, as discussed below. The wavelets extend across the spectrum of interest of a normal vestibular Sp/Ap response signal, and also include sufficient higher frequency components so that the peaks in the waveform can be well localised in time. Importantly, the bandwidth factor is set to less than 1, being 0.1 for the scales representing 1500 to 600 Hz and 0.4 for all remaining frequencies. Using a bandwidth factor that is so low allows for better time localisation at lower frequencies, at the cost of a frequency bandwidth spread, which is particularly advantageous for locating and determining neural events represented by the response signal. Magnitude and phase data is produced for each scale representing coefficients of the wavelets.

The phase data for each scale is unwrapped and differentiated (306) using the "unwrap" and "diff" functions of MATLAB. Any DC offset is removed, and the result is normalised for each scale to place it in a range from −1 to +1. This produces therefore normalised, zero average data providing a rate of phase change measurement for the response signal.

A first derivative of the phase change data (actually a derivative of a derivative) is obtained for each scale (308), and normalised in order to determine local maxima/minima rates of phase change (320). To eliminate any false peaks, very small maxima/minima are removed at a threshold of 1% of the mean absolute value of the first derivative (322). All positive slopes from the first derivative (308) are set to 1, negative slopes to −1 and then a second derivative of the phase change data is obtained (310) to produce −2 and +2 step values. Each scale is then processed to look for resulting values of −2 and +2 which represent points of inflexion for the determined maxima and minima (320). For these particular loci, a value of 1 is stored for all scales. For the low frequency scale, ie 600 Hz, the actual times for both the positive and negative peaks are also stored for analysis to further isolate the driven responses as discussed below.

The original response signal in the time domain (312) is also processed to detect points which may be points of maximum phase change for comparative analysis with the extracted phase peaks from the wavelet analysis. Firstly the mean and maximum of the original signal is determined. The signal is then adjusted to have a zero mean. Using this signal, the process locates and stores all points where the signal is greater than the mean minus 0.1 of the maximum in order to identify regions where an Ap point is least likely (positive deviations above axis) and to exclude in later derivatives maxima as a consequence of noise. The slope of the original response is obtained by taking the derivative of the original response, and then also determining the absolute mean of the slope. For the result obtained, all data representing a slope of less than 10% of the absolute mean slope is set to 0. A derivative is then obtained of this slope threshold data (314) which is used to define the local maxima/minima of the slope (316). Similarly, the absolute mean of this result is also obtained and a threshold of 10% of the mean used to exclude minor maxima/minima (step 318). All positive slopes of the original response are set to 1 and the negative slopes are set to −1, and then a second derivative obtained (314), From this derivative each scale is examined to find values of −2 and +2, representing points of inflexion. The position of these loci are stored for the positive and negative peaks.

For each scale, if there is a positive peak, ie a maximum, determined from the first slope derivative, then for any peaks corresponding to these times (+1 or −1) these are set to 0 in any scale in which they appear in order to initially selectively look for the Ap point which will be a minima. The same is also done for points that were previously deemed unlikely regions for an Ap point found during the original processing of the time domain response signal (312). The times of the peaks determined during processing of the phase data, and that determined during processing of the time domain signal, are compared (step 324). Because of scale dependant phase shifts inherent in detecting each wavelet scales phase maxima, the wavelet scale maxima are compared with those detected in the time domain and shifted to correspond to a magnitude minima in the time domain. Thus potential Ap loci (326) are determined.

The loci times for the low frequency scale, scale 7 representing 600 Hz, are searched to attempt to locate the Sp point, as it is most likely that the preceding steps have determined the Ap point, due to the size of the signal and the difficulty of normally locating the Sp point. This search is undertaken over a range of normally 0.1 to 0.9 ms (depending on the noise level; for example the lower limit of 0.1 may be increased, say to 0.5) before the potential Ap point looking for +2 values (i.e. negative peaks) in this range. If the value of the original response signal at the potential Sp point is greater than 0.9 of the potential Ap point (a negative value), then both the Ap loci and the potential Sp loci are stored. If an Sp point is located 0.1 to 0.9 ms before the Ap point, then the 600 Hz scale loci time for the Ap point and the time domain minima, proximal to that Ap point, are checked to determine whether they are at the same point in time. If this is not the case, then the scale loci is reset to match the time domain loci to take into account any limitations in time localisation properties associated with the wavelet decompositions. For verification, similar location procedures for the Sp point can be performed on the other scales, but this is not needed in all cases.

Figure 1:
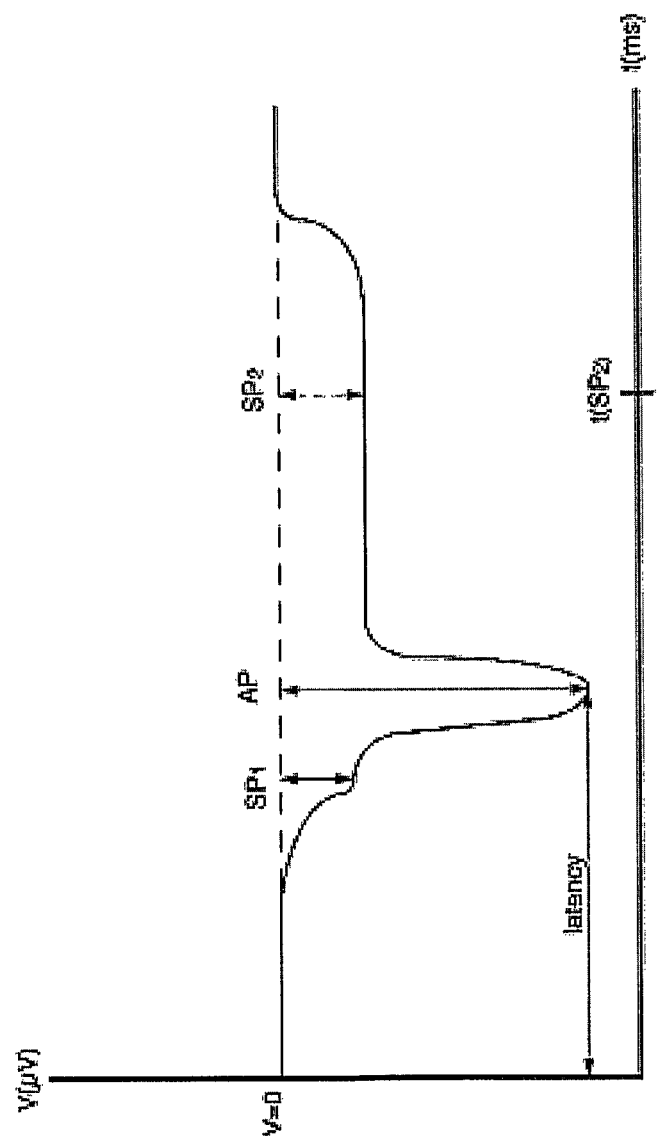
FIG. 1 is a representation of Sp, Ap and Sp2 points related to the first wave of a generalized ECOG response signal from an ECOG system and defines the summating potentials Sp and Sp2 and the action potential Ap.

All of the scales are then processed (step 330) to look for maxima across the scales and link them to form a chain across as small a time band as possible. This allows false Aps associated with all of the scales to be eliminated. The analysis module 28 is able to use a "Chain maximum-eliminate "false" maxima" routine of MATLAB® to perform this step. As described below, a Sp/Ap plot is formed by processing the time domain signal (or averaging the time domain signals obtained) centred on the local maxima determined previously. Following the Sp/Ap plot formation process, maxima/minima values are further determined to establish the baseline (ie the average level before the evoked response, as shown in FIG. 1) necessary to calculate the Sp/Ap.

Using firstly the +2 values, and then the −2 values if no +2 values are found, for the points of inflexion determined from the phase data, the loci is searched in the range allocated to the Sp previously determined (typically 0.5 to 0.9 ms before Ap). For each Ap, remaining after the elimination process (330) the Sp times are found and averaged to record an Sp.

The baseline is found (340) by starting at the Sp point −0.2 to −0.6 ms (based on average Sp/Ap shape), and again beginning with the +2 point inflexion values, and then −2 point inflexion values (if necessary) of the phase data in a time range initially allocated to the baseline. For each Sp plus offset, the potential baseline times are found and averaged to record an initial baseline time. If the baseline time does not meet a baseline check, then the process is repeated starting with the new baseline time estimate. This process is repeated until a baseline check is met, which may be whether a baseline is within a predetermined time range from the Ap and Sp. The average magnitude at the determined time is used. Alternatively, the baseline can be determined as being the mean of the first 300 samples of the Sp/Ap plot.

Sp2 is found (330) by also using firstly the +2 values for the points of inflexion of the phase data, and then if there a no +2 values using the −2 values, and searching for loci in the range allocated (initially 1.3 ms after the Ap). For each Ap plus offset, the Sp2 times are determined and then averaged to record an Sp2 time. The average magnitude at the determined time is used.

An artifact, being a spike of about 3 samples wide, is produced at the tip of Ap due to the selection of local minima in the time domain based on scale determined loci proximal thereto. The samples corresponding to the spike (which may be up to 5 samples) should be removed, and this is done (342) by using the values of the points on either side of the spike to interpolate values into the removed sample positions. A filter, such as a 15 point moving average filter, can then be applied after removal to smooth the response.

Based on the Sp, Sp2 and Ap neural events determined, the ratios Sp/Ap and Sp2/Ap are calculated and displayed with the plot of the vestibular response (350). The plot is generated by the display module 30 using the times/loci of the maxima and minima determined by the neural event extraction process.

In summary, the neural event extraction process uses a complex time frequency approach with a variable bandwidth factor to determine the points where maximum/minimum phase changes occur across a range of frequencies characteristic of neural events associated with an Sp/Ap plot. The maximum/minimum phase change is used to establish the Ap, Sp, Sp2 and baseline points. Being able to determine these points enables elimination of other phase change events that are not related to an Sp/Ap plot, such as those produced by background noise. Also, maximum/minimum phase change points are correlated with events in the time domain to reduce time localisation error inherent in the use of the frequency domain representation provided by the wavelet analysis.

Figure 5:
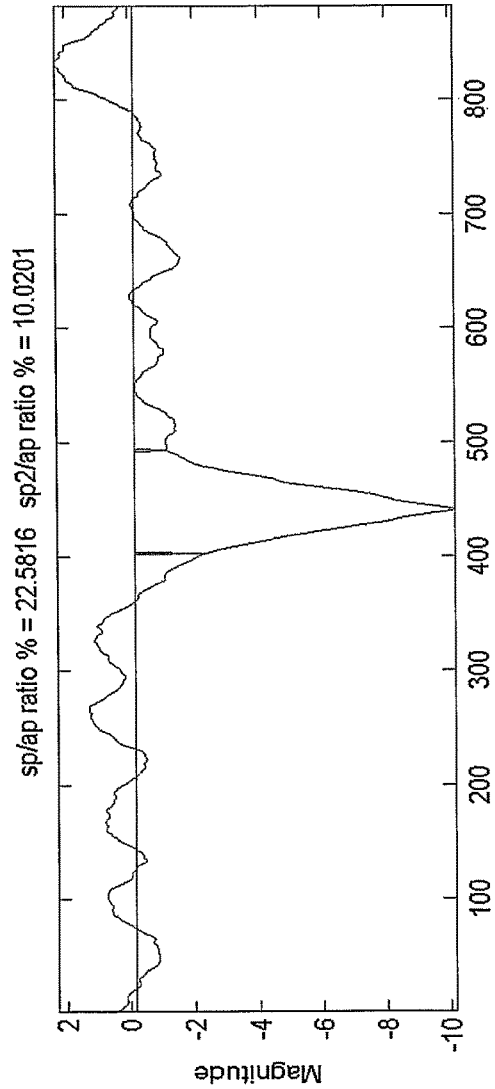
FIGS. 5 to 10 are Sp/Ap plots produced by the neural event process.
Figure 9:
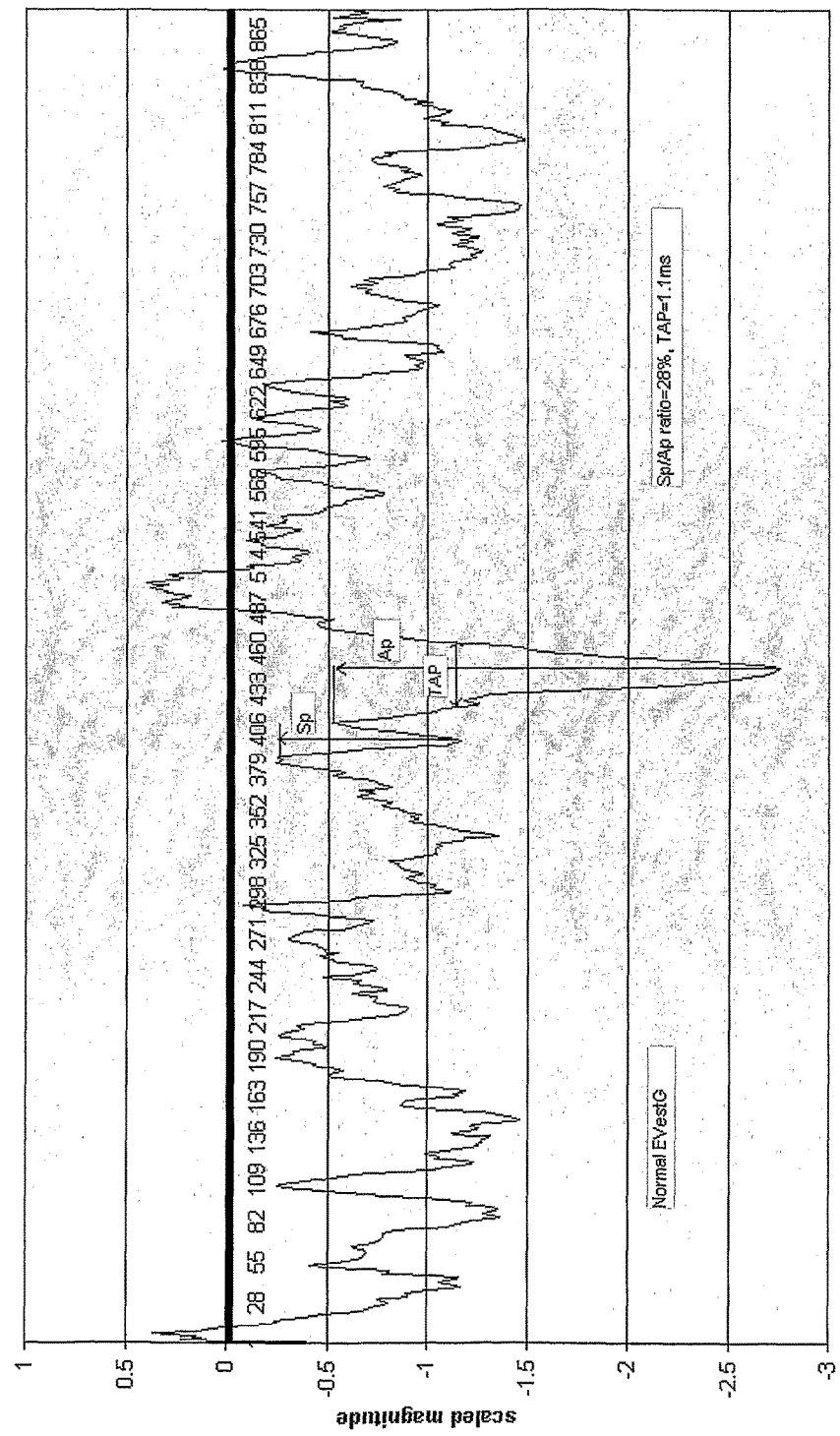

FIG. 5 shows an example of a display produced by the ECOG system 2 following analysis of a 1 second region of a steady state response (14.4 seconds after head tilt onset) to a voluntary backwards head tilt (patient's eyes open). The Sp/Ap ratio is determined to be 22.6% by the analysis module. The horizontal scale is 1 ms, equivalent to 44.1 samples of the evoked response signal. FIG. 9 shows a similar display produced following analysis of a 10 second region of a steady state response (10 seconds after head tilt onset) where the Sp/Ap ratio is determined to be 28%.

Figure 6:
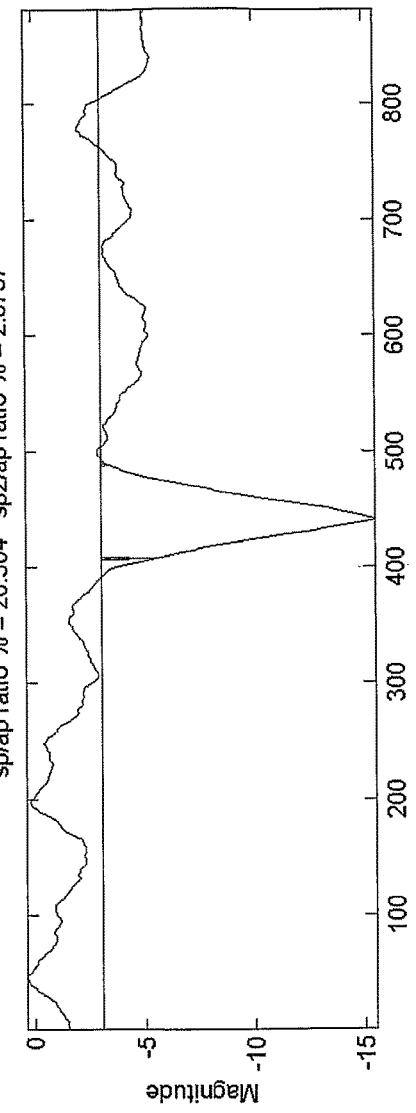
Figure 7:
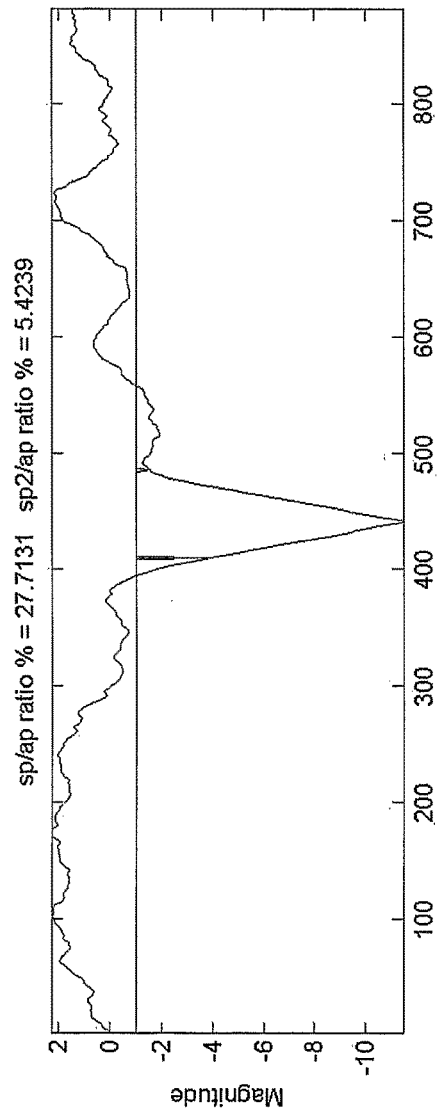
Figure 8:
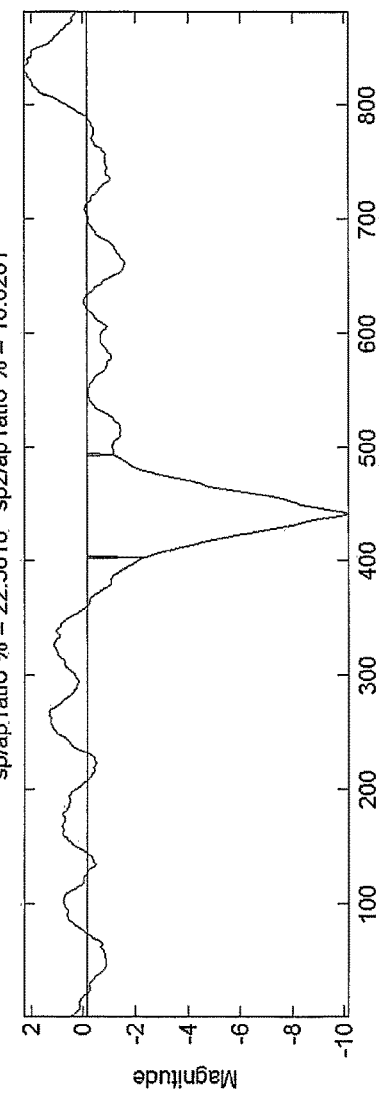

FIGS. 6, 7 and 8 also show Sp/Ap plots produced using the ECOG system 2. The plots are for a non voluntary movement on a tilt chair. FIG. 6 is a plot for the onset region, FIG. 7 is a plot for the transient region and FIG. 8 is a plot for the steady state region.

Figure 10:
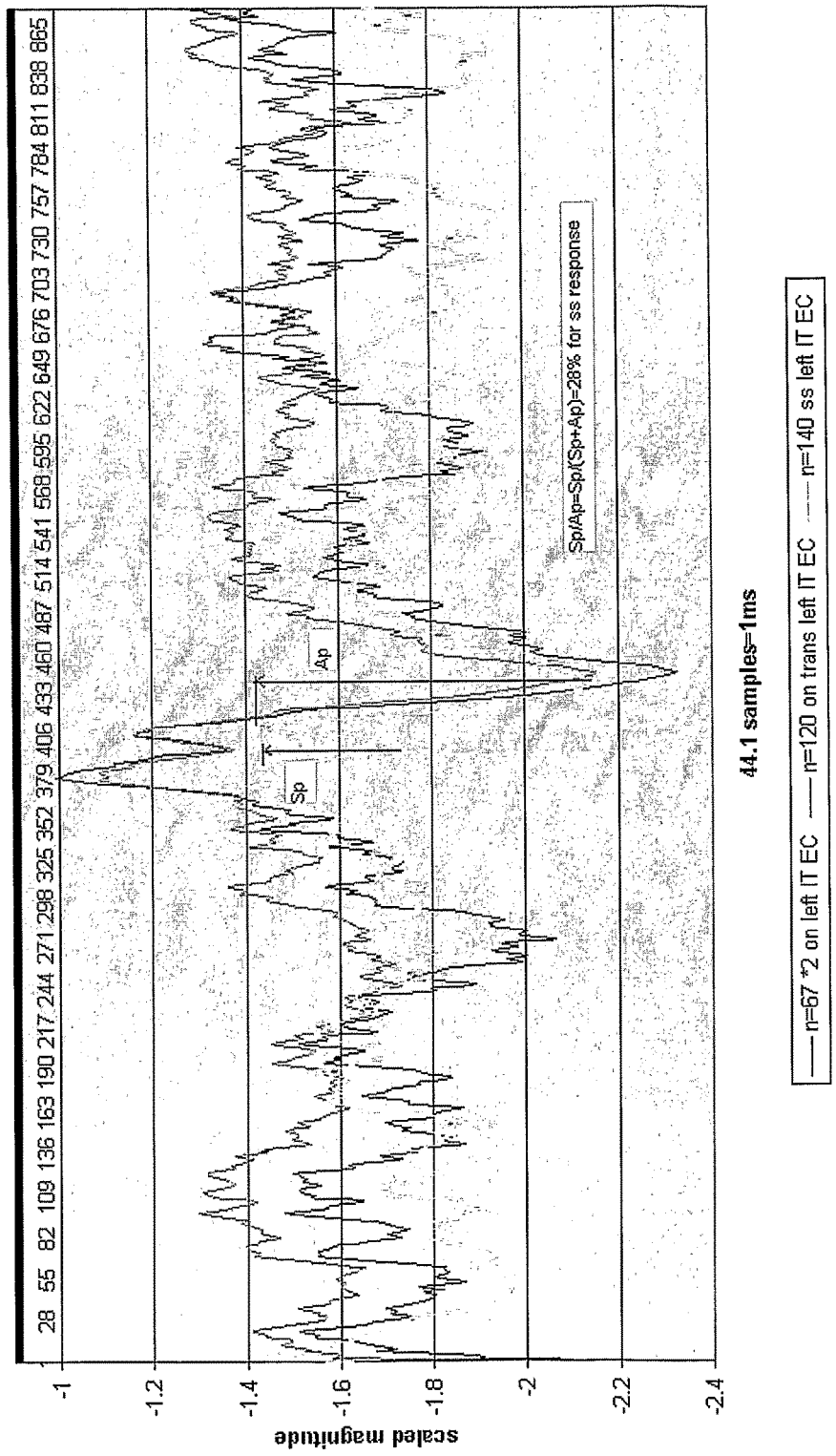

All the plots have a baseline, Ap and Sp (and Sp2 seen normally only with tone stimulus responses and also for the onset period or component of excitatory tilt responses) point marks that can be determined by the neural event extraction process of the analysis module 28. FIG. 10 also shows Sp/Ap plots produced for the onset region (dark), steady state region (light) and for the transient region (medium). In this Figure, the Sp and Ap is shown as only that determined for the steady state response.

The system 2 as described is able to perform an accurate analysis of a response from the vestibule that not only can be used for the detection of Meniere's disease, but can also be used for diagnosis of Parkinson's disease and depression as discussed below. Also other neural events can be sought and determined, such as those produced by other auditory nuclei. The system 2 can be configured to obtain other AERs and the analysis module 28 used to accurately process the AER obtained, such as an ABR.

Latency considerations relevant to the Auditory Brainstem Response (ABR) allow for the separation then generation of Sp/Ap like waveforms from each main nuclei. Responses from subnuclei like the Medial Nucleus of the Trapezoid Body, Lateral Superior olive and Medial superior olive of the superior olivary complex are also separable. Responses could also be obtained from the visual pathway and its nuclei, indeed most evoked response pathways.

For the ABR, the system 2 is adjusted so the analysis module 28 executes an ABR process, as shown in FIG. 13, and the electrodes 10 and 12 are rearranged to obtain an ABR response, instead of an ECOG response. In particular, the patient 4, remains at rest, and the electrodes 10 and 12 are used as surface electrodes, with one being placed on each mastoid, and the additional electrode 14 used on the forehead. The patient's leg is again connected to the shield 18. The stimulus produced by the computer system 20 is an audible click (100 us) or tone pip (5 ms), eg 80 dB SPL (sound pressure level), repeated about 300-1000 times. Each stimulus is 200 ms apart. The first 10 ms post stimulus is recorded. The ABR process, as shown in FIG. 13, is primarily the same as the neural event process described above with reference to FIG. 4, except for the following:

(i) The first stage of the process (302) performs segmentation by recording the 10 ms of interest from the 200 ms of each response signal received. The recorded 10 ms time domain signal is then filtered using a 500 Hz-4 kHz bandpass 6 pole Butterworth filter.

(ii) The wavelet scales used in the step 304 have the same bandwidth factors, except a very small bandwidth factor of 0.05 is used for the lowest frequency scale, 600 Hz.

(iii) Additional processing (802) is performed after step 330 to determine the Ap point marks corresponding to each of the subnuclei of interest. This is done on the basis of the latencies of the Aps in comparison with the time domain data in order to construct an Sp/Ap plot for the nuclei and subnuclei of interest, eg 3.2 ms to 4.4 ms for peak III of an ABR.

Figure 14:
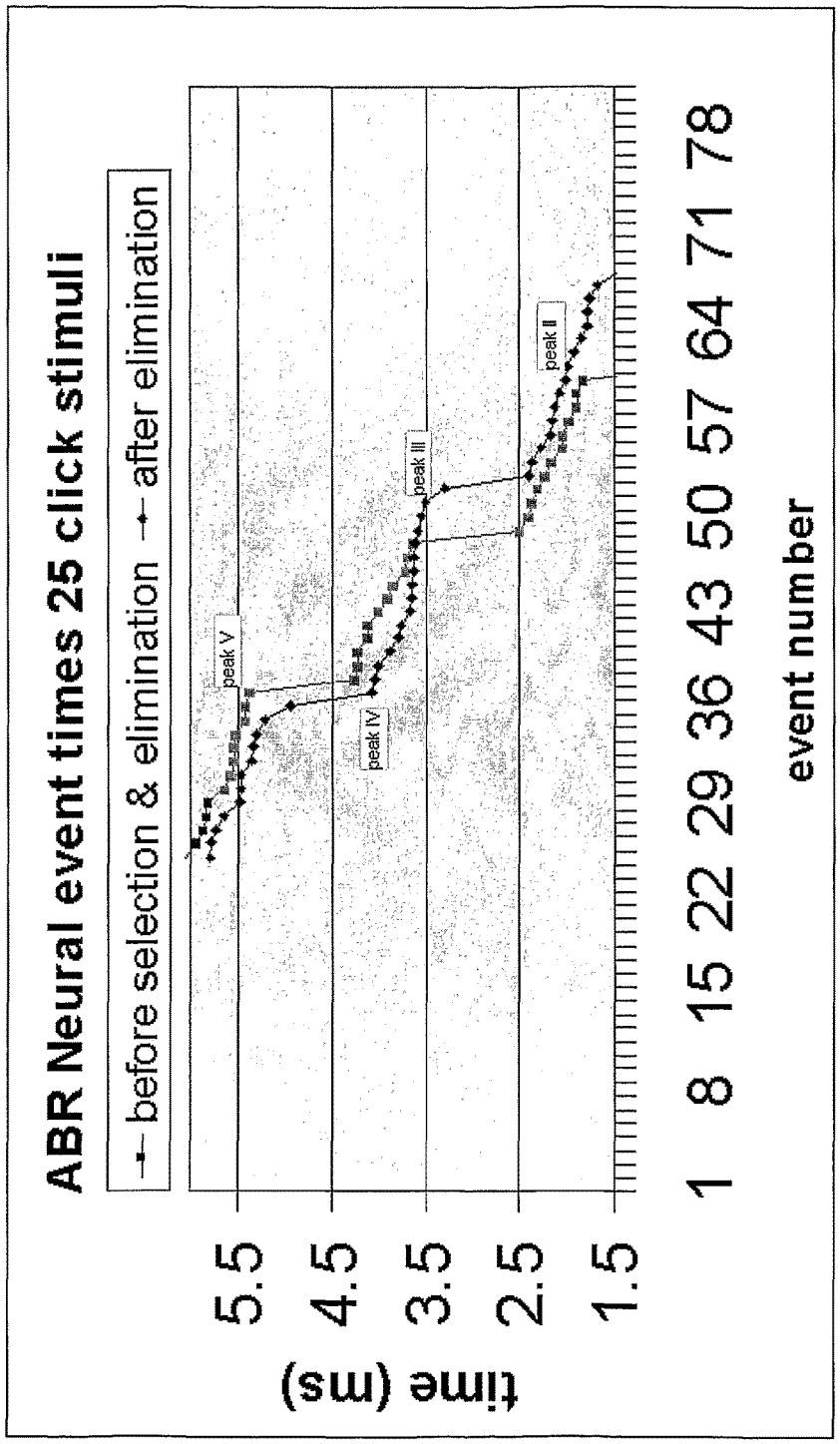
FIG. 14 is a display produced by the ABR system of detected ABR neural events.
Figure 15:
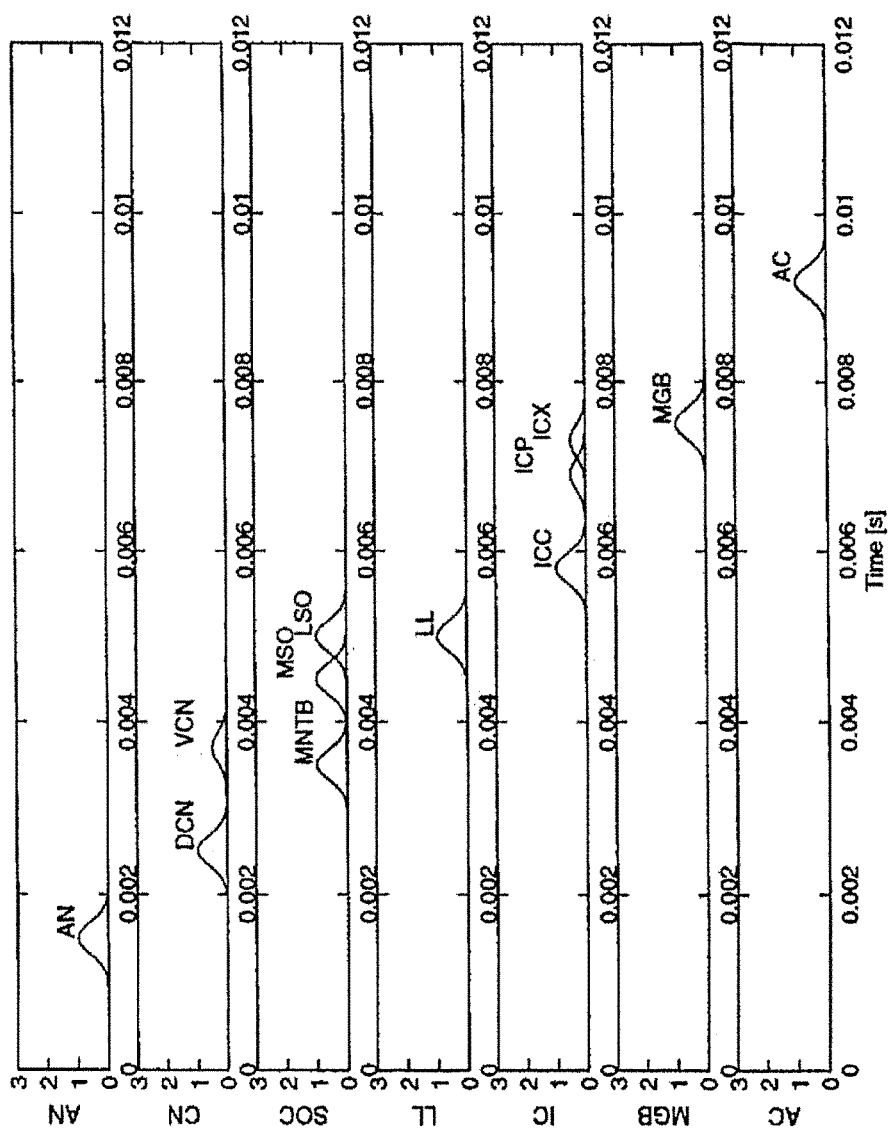
FIG. 15 is a diagram of different ABR components.

FIG. 14 is a display produced of a plot showing the neural events detected by the system 2 from 25 ABR stimulus recordings, with the neural events corresponding to peaks II to V of an ABR delineated. The data for each of the detected neural events, at times associated with the events, can be averaged to produce Sp/Ap plots for the nucleus of interest. FIG. 15 illustrates the timing, ie the latency, of the different ABR components for the different nuclei and subnuclei, which include the auditory nerve (AN), the dorsal cochlea nucleus (DCN), ventral cochlea nucleus (VCN), medial nucleus of trapezoid body (MNTB), lateral superior olive (LSO), medial superior olive (MSO), lateral lemniscus (LL), central nucleus of inferior colliculus (ICC), pericentral nucleus of inferior colliculus (ICP), external nucleus of inferior colliculus (ICX) and medial geniculate body (MGB). The responses from the nuclei and subnuclei are separable into different events as shown in FIG. 14. Using a tone instead of a click enables a response to be evoked from the lamina in the nucleus of interest. The neural event detected using a click is a response from the entire tonotopic region of the nucleus. However by using a tone only, one lamina or layer of the nucleus is excited allowing for the localisation within the nucleus of any departures from a normal response.

Figure 16:
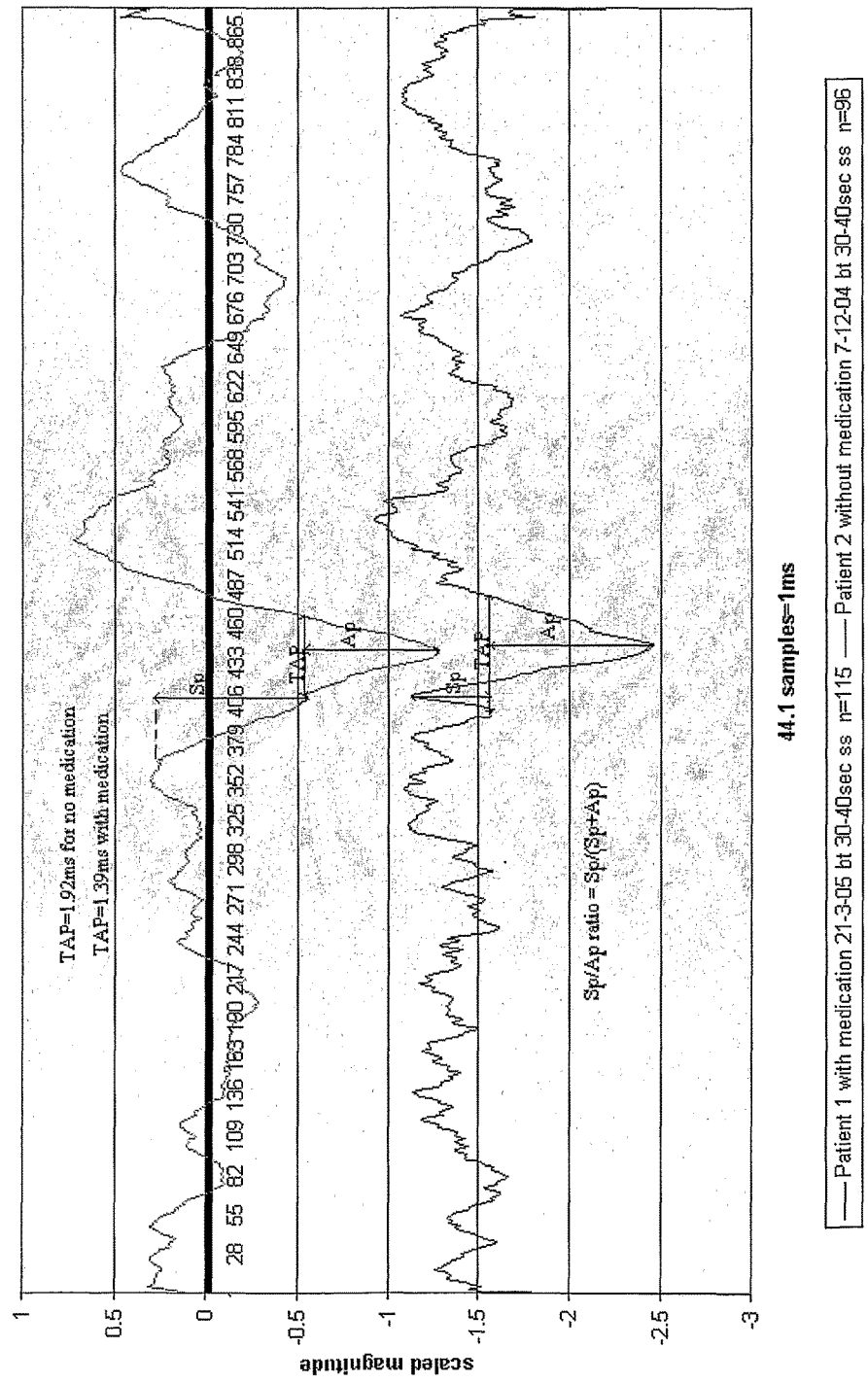
FIG. 16 is a display of Sp/Ap plots for a Parkinson's patient produced by the ECOG system.

A further application of the ECOG system 2 is detecting the degeneration of cells in the Basal Ganglia (eg Substantia Nigra in Parkinson's Disease) by accurately detecting the 70-300 Hz inter-event intervals (time-frequency representations) and changes in the neural Sp/Ap response characteristics (including Ap width, Sp peak height, etc) consequent to changes in the Basal Ganglia and other connected structures observed in the vestibular response and believed to be modulated by Basal Ganglia outputs via the reticular formation to the vestibular nuclei. This is particularly useful for quantitatively measuring the efficacy of therapies and drugs to treat, as well as for the early detection of, Parkinson's disease. FIG. 16 shows two Sp/Ap plots produced by the system 2 for a Parkinsons patient, one where the patient is without medication (upper), and another where the patient is with levodopa medication (lower with a deliberate offset for clarity). The effect of the medication is indicated by the Ap width, ie the TAP measurement, the Sp magnitude change and the general change in the Sp/Ap plots. The TAP is a time measure from the minima peak ("notch") before the Sp peak horizontally to the upward arm of the Ap, as shown in FIG. 16. Alternatively, a different TAP measure could be the internal width of the Ap horizontally at the Sp notch vertical level used in the preceding definition.

Figure 17:
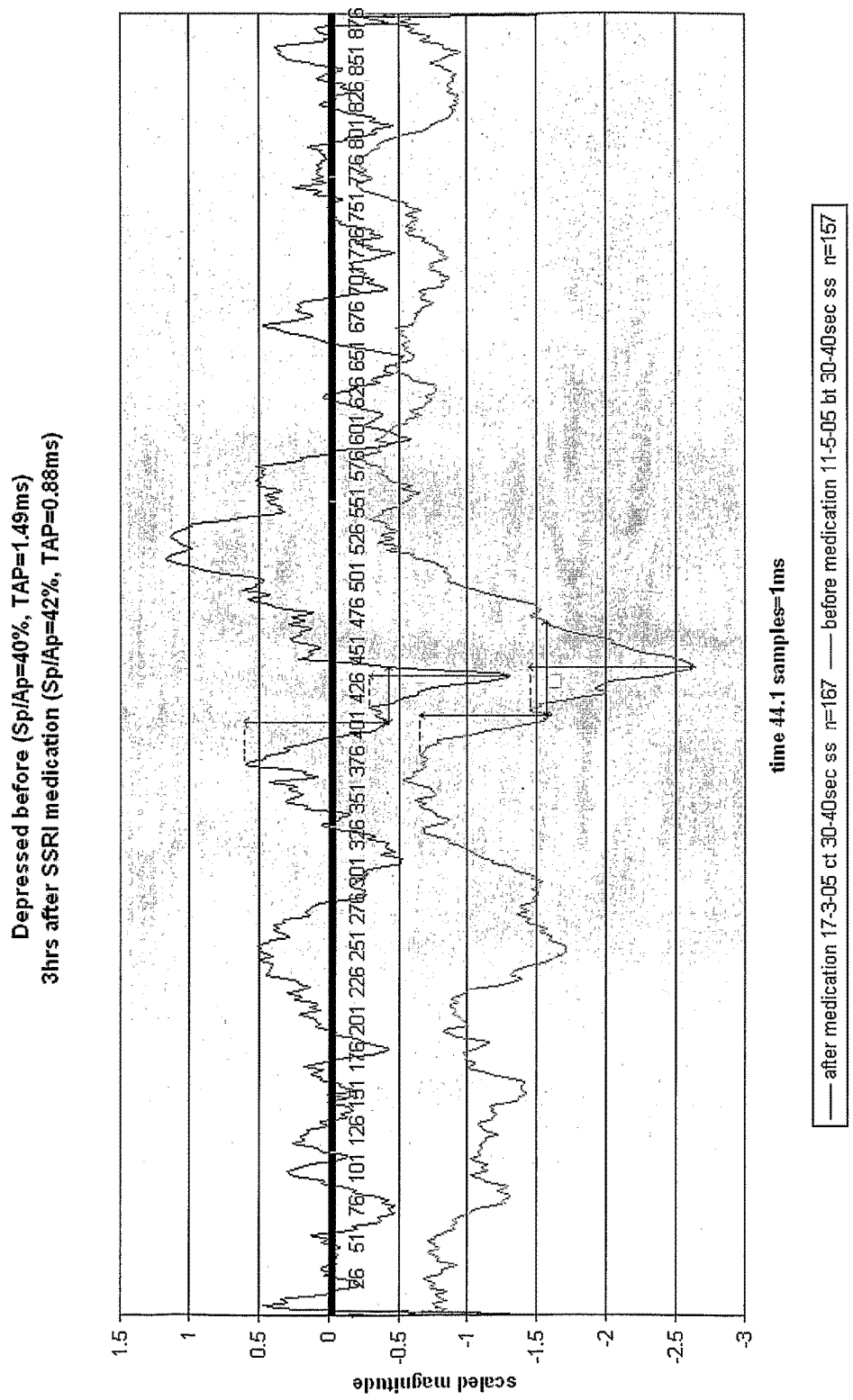
FIG. 17 is a display of Sp/Ap plots produced for a patient suffering depression by the system.

Another application is detecting the decrease or increase in activity of cells in the Basal Ganglia (eg Thalmus in depression) co-incident with changes in depressive state by again accurately detecting changes in the 70-300 Hz inter-event intervals (time-frequency representations) and changes in the neural Sp/Ap response characteristics (including Ap width, Sp peak height, etc) consequent to changes in the Basal Ganglia and other connected structures observed in the vestibular response and believed to be modulated by Basal Ganglia outputs via the reticular formation to the vestibular nuclei. This is particularly useful for quantitatively measuring the efficacy of therapies and drugs to treat depression, as well as the detection of depression (particularly in intellectually disabled and those with limited communication skills). FIG. 17 shows two Sp/Ap plots produced by the system 2 for a patient suffering depression. One plot is before the patient is medicated (lower and light), and the second plot has been taken three hours after the patient has been medicated with SSRIs (Selective Serotonum Uptake Inhibitors) (upper and dark). Again, the effect of the medication is indicated especially by the Ap width, ie the TAP measurement marker.

Figure 18:
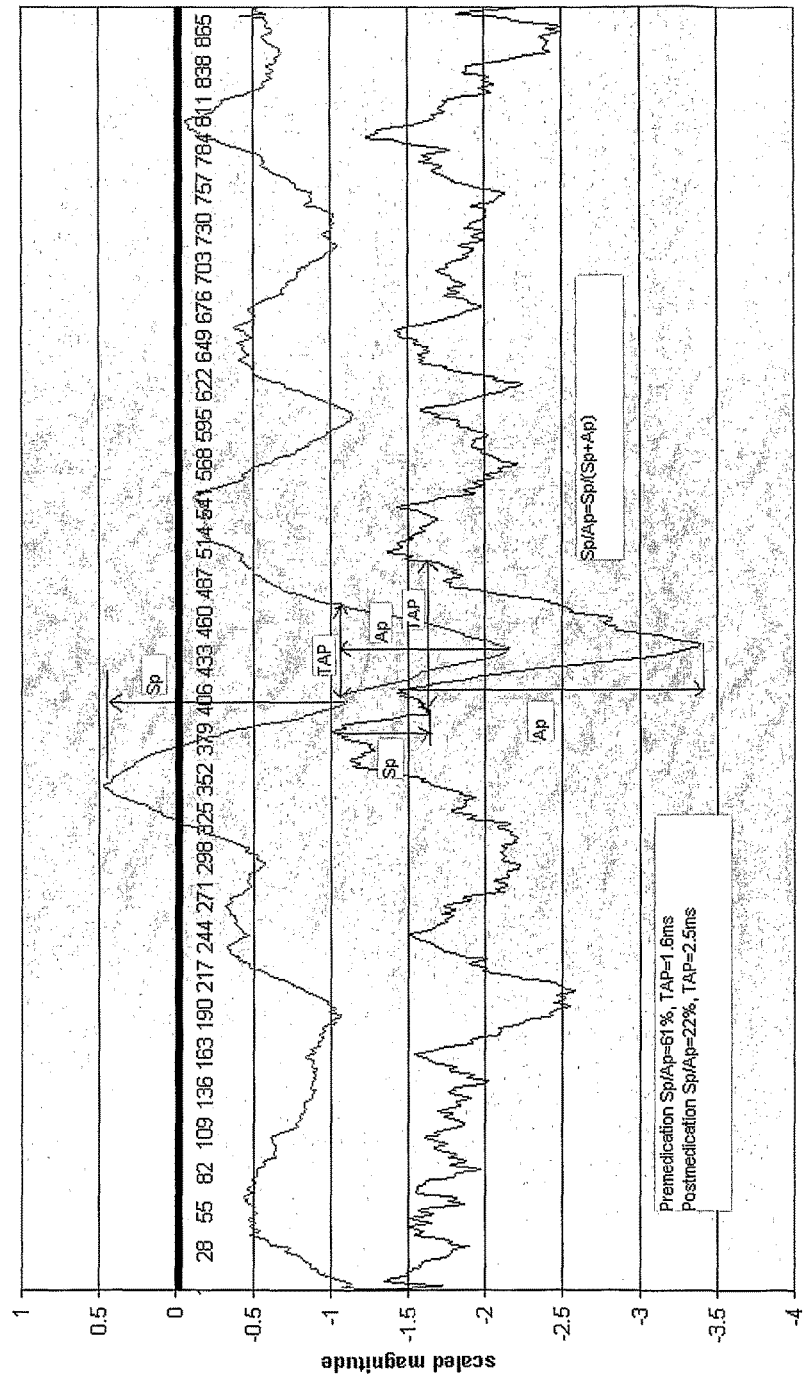
FIGS. 18 and 19 are displays of Sp/Ap plots produced for a Meniere's patient by the system.
Figure 19:
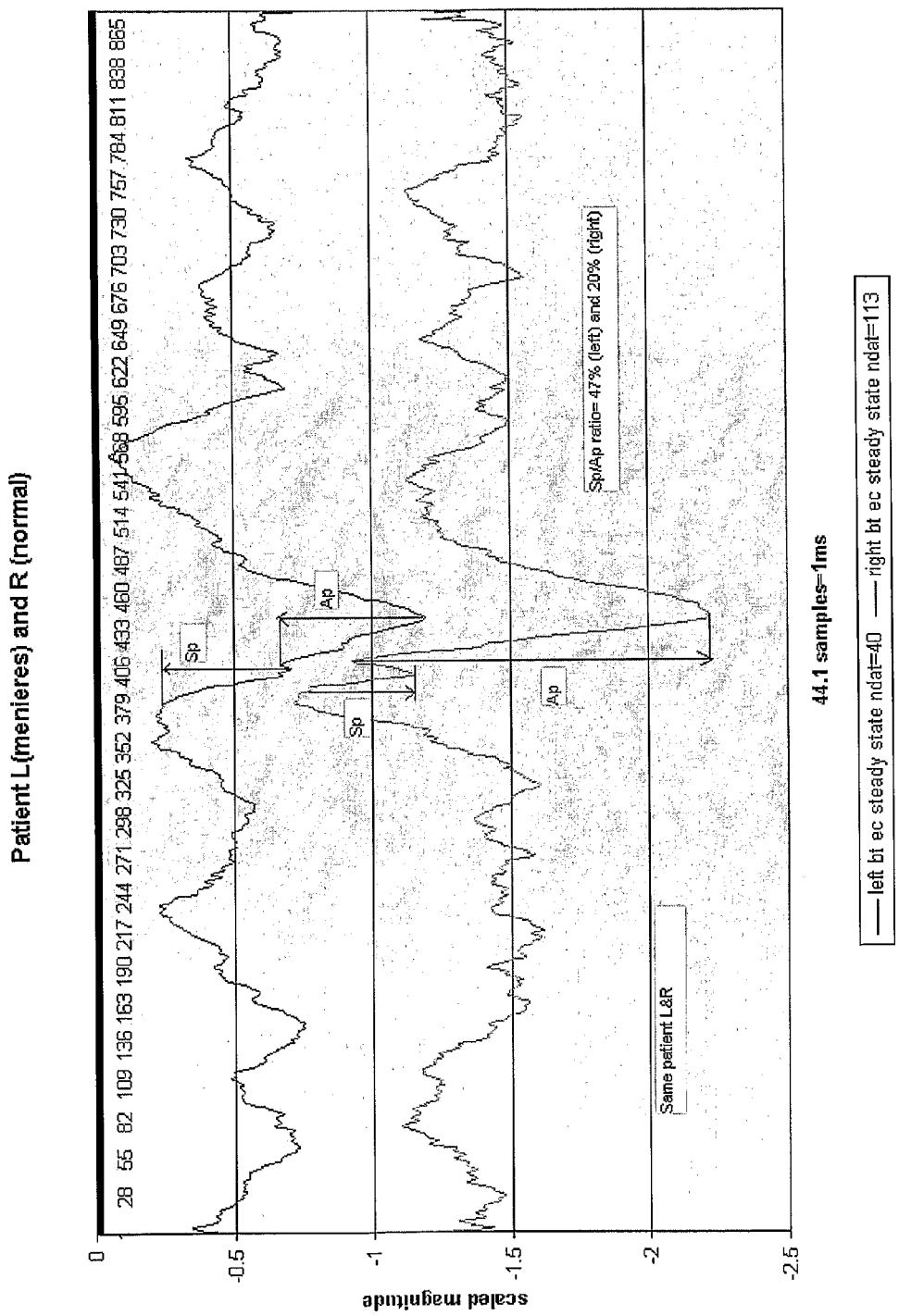
Figure 20:
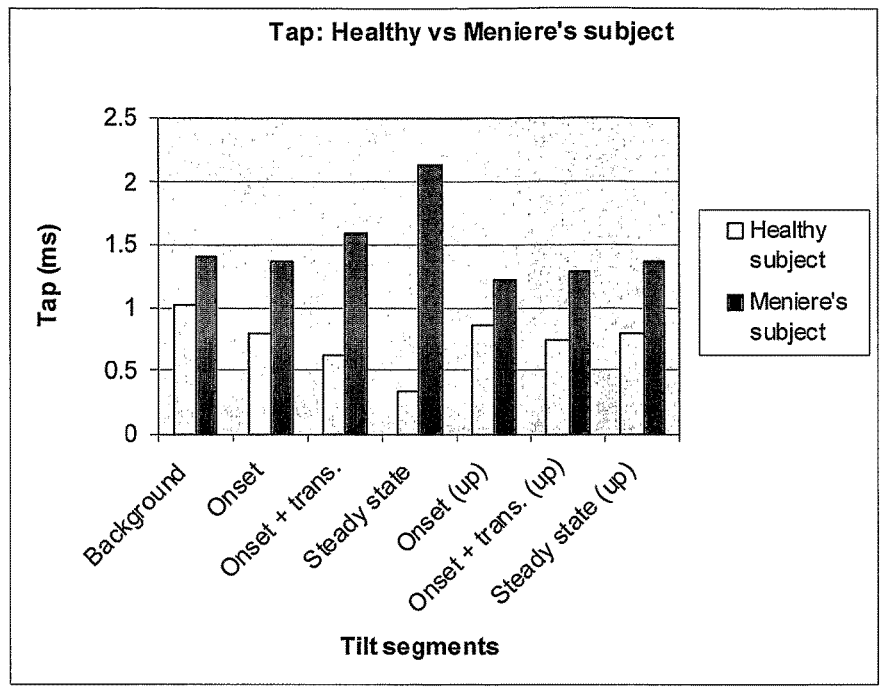
FIGS. 20 to 24 are displays of TAP measurement markers produced by the system for a number of patients.
Figure 21:
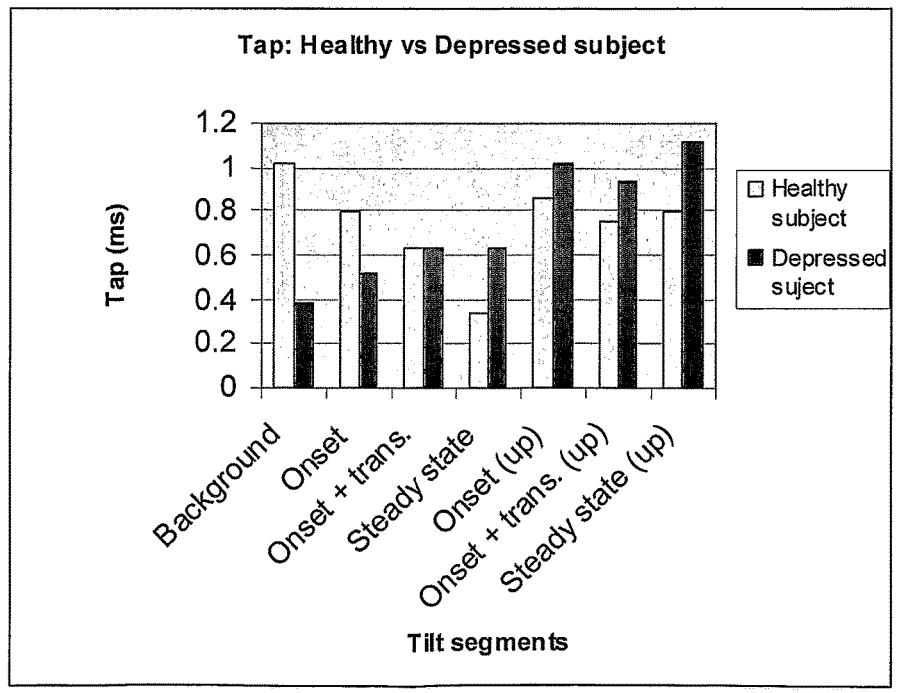
Figure 22:
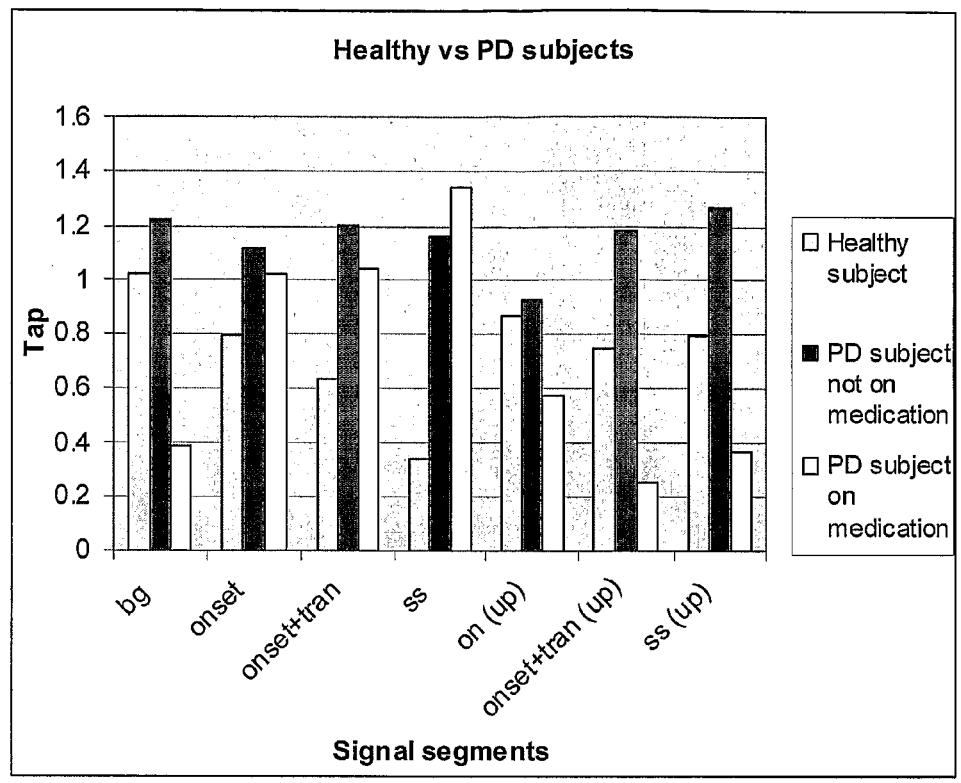
Figure 23:
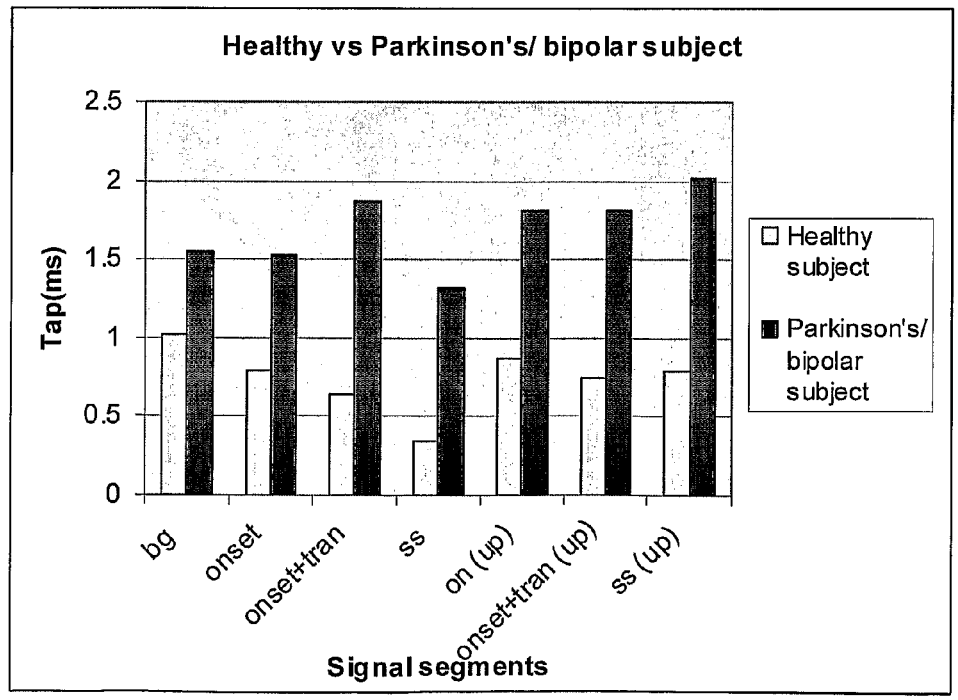
Figure 24:
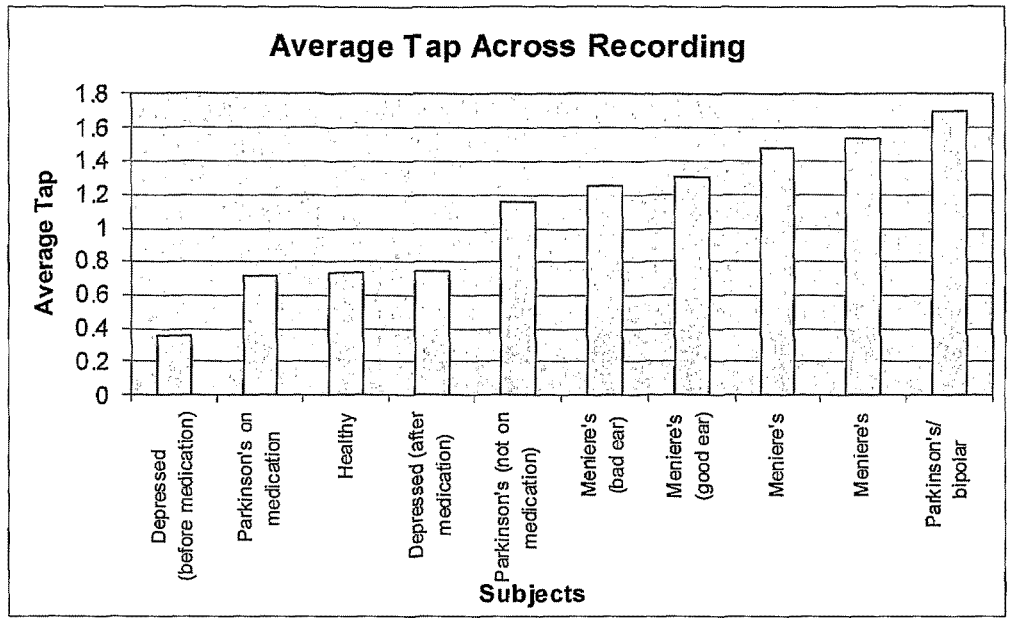

FIG. 18 shows an Sp/Ap plot produced by the system for a Meniere's patient with (lower) and without medication (upper), this again shows the stark differences between the Sp/Ap plots, and the Ap width measure, TAP. The medication used was AVIL™ (43.5 mg). FIG. 19 shows Sp/Ap plots comparing a Meniere's patient with symptoms on the left side (upper) but not on the right side (lower).

Figure 25:
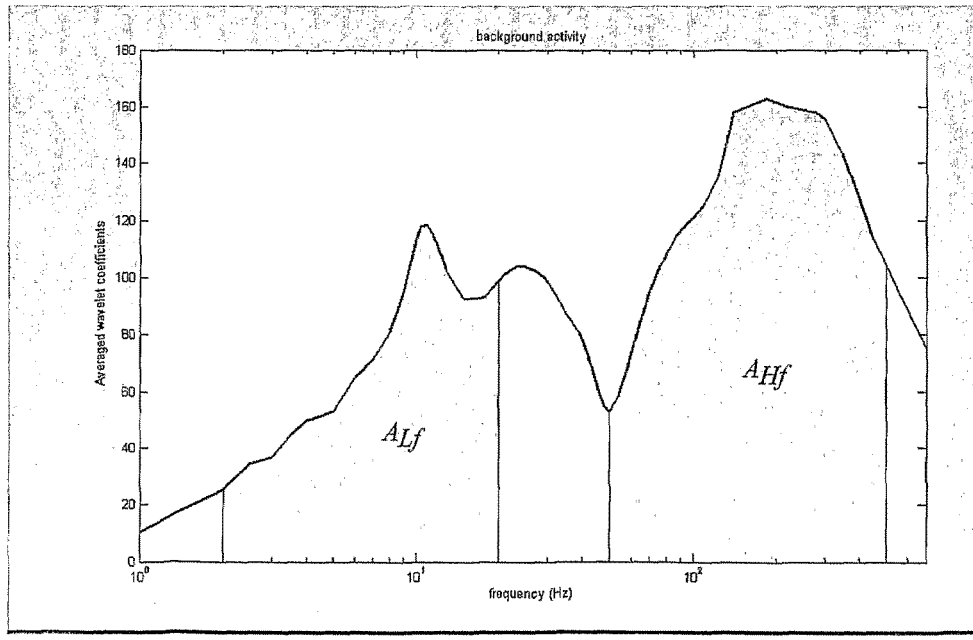
FIG. 25 is a diagram of averaged wavelet coefficients against frequency generated by the system.
Figure 26:
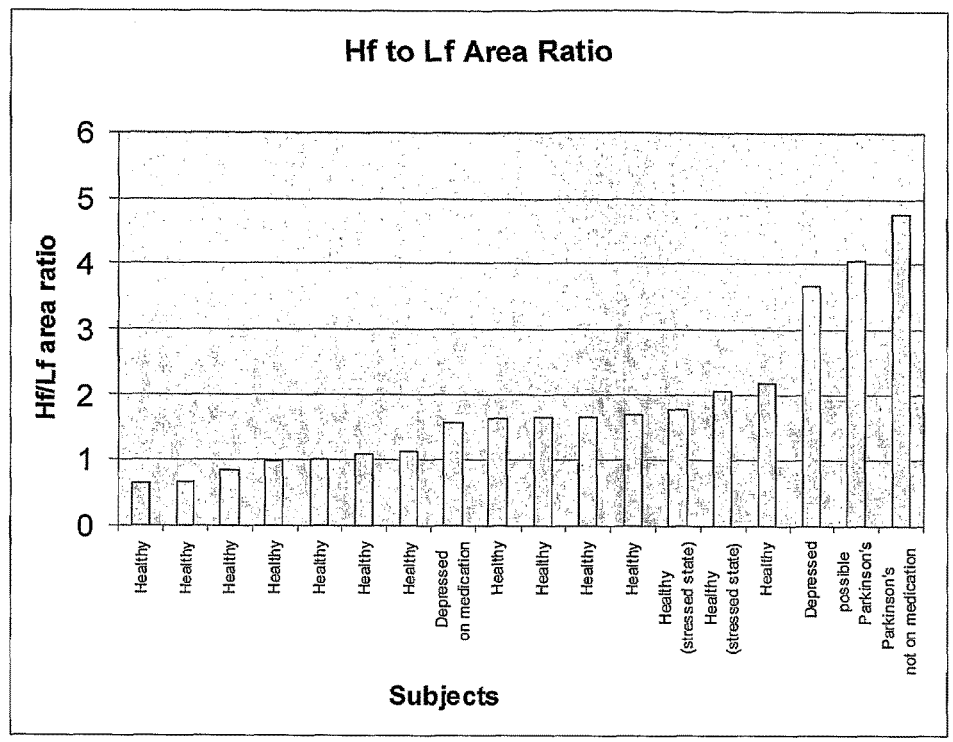
FIG. 26 is a display of HF/LF ratio data markers produced for a number of different patients by the system.

The analysis module 28 of the system 2 is able to produce a series of markers to discriminate between patients that have, or to determine whether they have, a disorder, such as a central nervous system (CNS) disorder, and in particular whether they are depressed, suffering Meniere's disease, or suffering Parkinson's disease. The markers include (i) the Sp/Ap point marks, (ii) the TAP measurement, being the time and duration of Ap (plus the Sp peak depending on the TAP period definition used), and (iii) a HF/LF ratio being the ratio of the high frequency energy to the low frequency energy of the average wavelet coefficients of the scales, as shown in FIG. 25. The HF/LF ratio is a ratio for the response signal of the high frequency and low frequency areas beneath the plot of the averaged wavelet coefficients against frequency for the respective ranges 50 to 500 Hz and 2 to 28 Hz, as shown in FIG. 25. FIGS. 20 to 24 show a variety of TAP measurements obtained for different patients, and illustrate how they can be discriminated. FIG. 26 shows how the HF/LF ratio can be used as a discriminating marker. Other markers are provided by analysis of scales for the 70 to 300 Hz range to determine alterations to the response signal and Sp/Ap plots due to modulation by the Basal Ganglia components. The alterations may be the presence or absence of peaks or distribution changes for time against frequency representations for this range. Peaks within this range, particularly proximal the ranges 70-90 Hz, 110-150 Hz and 200-300 Hz, may indicate activity of the Basal Ganglia components. If those markers are used, additional scales are used by the neural event process for the 70 to 300 Hz range.

To assist diagnosis, the magnitude, phase, frequency and time data extracted by the neural event process can be used to generate three dimensional or four dimensional (with color) plots for responses obtained from patients.

Many modifications will be apparent to those skilled in the art without departing from the scope of the present invention as herein described with reference to the accompanying drawings.

The invention claimed is:

1. A neural event process, executed by a computer device, including:
   receiving an electrovestibulography (EVestG) signal associated with a person;
   decomposing said signal using wavelets;
   obtaining derivatives of phase data of said wavelets using the computer device; obtaining derivatives of said response signal;
   determining maxima and minima of said phase data using the derivatives of said phase data;
   determining maxima and minima of said response signal using the derivatives of said response signal;
   processing said maxima and minima of said phase data and said maxima and minima of said response signal with the computing device to extract timing information to determine peaks representing neural events;
   wherein said obtaining derivatives of phase data includes generating first and second derivatives of said phase data produced by said decomposing, and said maxima and minima of said phase data represent rate of change of phase of scales of said wavelets; and
   wherein said maxima and minima of said phase data and said response signal are used to generate data indicating whether said person has a central nervous system disorder.

2. A neural event process as claimed in claim 1, wherein said decomposing is performed using said wavelets with a bandwidth factor less than one.

3. A neural event process as claimed in claim 2, wherein said wavelets have centre frequencies across a frequency spectrum of said signal.

4. A neural event process as claimed in claim 1, wherein said obtaining derivatives of said response signal includes generating first and second derivatives of said response signal to produce said maxima and minima of said response signal, and said processing includes correlating said maxima and minima of said phase data and said maxima and minima of said response signal based on time data for said maxima and minima of said response signal.

5. A neural event process as claimed in claim 4, wherein said processing includes eliminating false peaks by applying threshold data to said maxima and minima of said phase data and said response signal.

6. A neural event process as claimed in claim 5, wherein said correlating includes linking said maxima of said phase data across said scales and across a time band to eliminate false peaks.

7. A neural event process as claimed in claim 6, wherein said processing includes applying predetermined latency ranges for said peaks to said maxima and minima of said phase data to determine said peaks.

8. A neural event process as claimed in claim 7, wherein said receiving includes filtering and sampling said response signal for said decomposing, differentiating and processing.

9. A neural event process as claimed in claim 2, wherein said bandwidth factor is between 0.05 and 0.4.

10. A neural event process as claimed in claim 9, wherein said bandwidth factor is 0.1 for low frequency scales and 0.4 for other scales.

11. A neural event process as claimed in claim 9, wherein said bandwidth factor is 0.05 for the lowest frequency scale.

12. A neural event process as claimed in claim 8, including removing at least one artefact from said response signal.

13. A neural event process as claimed in claim 1, wherein said neural events are represented by summating potential (Sp) and action potential (Ap) markers corresponding to said peaks.

14. A neural event process as claimed in claim 1, wherein said maxima and minima of said phase data and said signal are compared to generate a summating potential (Sp)/action potential (Ap) plot.

15. A neural event process as claimed in claim 1, wherein said EVestG signal is produced by a EVestG system in response to a head tilt of the person.

16. A neural event process as claimed in claim 15, wherein said maxima and minima of said phase data and said response signal are used to generate data indicating a response by said person to medication for a central nervous system disorder.

17. A neural event process as claimed in claim 15, wherein said maxima and minima of said phase data and said response signal are used to generate data indicating whether said person has Meniere's disease.

18. A neural event process as claimed in claim 15, wherein said maxima and minima of said phase data and said response signal are used to generate data indicating a response by said person to medication for Meniere's disease.

19. A neural event process as claimed in claim 15, wherein said maxima and minima of said phase data and said response signal are used to generate data indicating whether said person has Parkinson's disease.

20. A neural event process as claimed in claim 15, wherein said maxima and minima of said phase data and said response signal are used to generate data indicating a response by said person to medication for Parkinson's disease.

21. A neural event process as claimed in claim 15, wherein said maxima and minima of said phase data and said response signal are used to generate data indicating whether said person has depression.

22. A neural event process as claimed in claim 15, wherein said maxima and minima of said phase data and said response signal are used to generate data indicating a response by said person to medication for depression.

23. A neural event process as claimed in claim 1, wherein said maxima and minima of said phase data and said response signal represents a response obtained directly from the vestibular system of the person.

24. A neural event process as claimed in claim 1, wherein said maxima and minima of said phase data and said response signal represent components of the vestibular system.

25. A neural event process as claimed in claim 1, wherein said maxima and minima of said phase data and said response signal represents a response obtained directly from auditory nuclei and subnuclei of the ear of the person.

26. A neural event process, executed by a computer device, including: receiving a neural response signal associated with a person and produced by an electrocochleography system; decomposing said signal using at least one wavelet representing a centre frequency having a low frequency in the spectrum of said signal, said wavelet having a bandwidth factor greater than or equal to 0.05 and less than 1; obtaining derivatives of phase data of said wavelet using the computer device; obtaining derivatives of said response signal; determining maxima and minima of said phase data using the derivatives of said phase data; determining maxima and minima of said response signal using the derivatives of said response signal; and processing said maxima and minima of said phase data and said maxima and minima of said response signal to extract timing information to determine summating potential (Sp) and action potential (Ap) data; wherein said obtaining derivatives of phase data includes generating first and second derivatives of said phase data produced by said decomposing, and said maxima and minima of said phase data represent rate of change of phase of scales of said wavelets; and wherein said maxima and minima of said phase data and said response signal are used to generate data indicating whether said person has a central nervous system disorder.

27. A neural event process, executed by a computer device, including: receiving an auditory brain stem response (ABR) signal associated with a person and produced by an ABR system; decomposing said signal using at least one wavelet representing a centre frequency having a low frequency in the spectrum of said signal, said wavelet having a small bandwidth factor; obtaining derivatives of phase data of said wavelet using the computer device; obtaining derivatives of said response signal; determining maxima and minima of said phase data using the derivatives of said phase data; determining maxima and minima of said response signal using the derivatives of said response signal; and processing said maxima and minima of said phase data and said maxima and minima of said response signal to extract timing information to determine peaks representing neural events; wherein said obtaining derivatives of phase data includes generating first and second derivatives of said phase data produced by said decomposing, and said maxima and minima of said phase data represent rate of change of phase of scales of said wavelets; and wherein said maxima and minima of said phase data and said response signal are used to generate data indicating whether said person has a central nervous system disorder.

28. A neural event process as claimed in claim 24, wherein said neural events represent auditory nuclei and subnuclei.

29. A neural event response process as claimed in claim 27, wherein said bandwidth factor is 0.05 for the lowest frequency scale.

30. A computer readable storage device storing computer program code, which when executed by a processing device causes the processing device to perform the process as claimed in claim 1.

* * * * *